US006555108B1

(12) United States Patent
Breakefield et al.

(10) Patent No.: US 6,555,108 B1
(45) Date of Patent: *Apr. 29, 2003

(54) IMPLANTING HSV-TK RETROVIRUS PRODUCING CELLS TO TREAT TUMORS

(75) Inventors: Xandra O. Breakefield, Newton, MA (US); Robert L. Martuza, Chevy Chase, MD (US); Marion Priscilla Short, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/462,508

(22) Filed: Jun. 5, 1995

Related U.S. Application Data

(63) Continuation of application No. 07/895,364, filed on Jun. 9, 1992, now abandoned, which is a continuation-in-part of application No. 07/746,655, filed on Aug. 16, 1991, now abandoned, which is a continuation-in-part of application No. 07/582,055, filed on Sep. 14, 1990, now abandoned.

(51) Int. Cl.$^7$ .................. A01N 63/00; A61K 48/00; A61K 31/70

(52) U.S. Cl. ................. 424/93.21; 424/93.2; 514/44

(58) Field of Search .................. 424/93.2, 93.21; 514/44

(56) References Cited

U.S. PATENT DOCUMENTS 5,529,745 A * 6/1996 Barba et al.

FOREIGN PATENT DOCUMENTS

| EP | 0334301 A1 * | 9/1989 | ............ C12N/7/00 |
|---|---|---|---|
| WO | WO 90/07936 A1 * | 7/1990 | ............ A61K/39/12 |
| WO | WO 91/02805 A2 * | 3/1991 | ............ C12N/15/86 |
| WO | WO 95/06486 | 3/1995 | |

OTHER PUBLICATIONS

Markowitz, D. et al., "A Safe Packaging Line for Gene Transfer: Separating Viral Genes on Two Different Plasmids," *J. Virol.* 62: 1120–1124 (1988).*
Blaese et al (1994) Eu. J. Canc. 30A, 1190–1193.*
Mullen (1994) Pharmac. Therap. 63, 199–207.*
Freeman et al (1993) Cancer Res. 53, 5274–5283.*
Austin, F.C. and Boone, C.W., "Virus Augmentation of the Antigenicity of Tumor Cell Extracts," *Adv. Cancer Res.* 30:301–345 (1979).
Baker et al., "Suppression of Human Colorectal Carcinoma Cell Growth by Wild–Type p53," *Science* 249:912–915 (Aug. 24, 1990).
Barker et al., "Cloning and Sequence Analysis of the Human Gene Encoding Eosinophil Major Basic Protein," *Gene* 86:285–289 (1990).

Amano et al., "High Activity of Choline Acetyltransferase Induced in Neuroblastoma x Glia Hybrid Cells," *Exptl. Cell Res.* 85:399–408 (1974).
Angier, N. "Tumor Treatment Showing Promise," *N.Y. Times, National Edition*, p. B11 (Sep. 8, 1993).
Araki et al., "The Essential Region for Assembly and Particle Formation in Hepatitis B Virus Surface Antigen Produced in Yeast Cells," *Gene* 89:195–201 (1990).
Berends et al., "The Detection of Virally Induced Tumors by $^{131}$I– and $^{125}$I–Labeled Syngeneic Monoclonal Antibodies," *Cancer Immunol. Immunother.* 26:243–249 (1988).
Bernstein et al., "Genetic Ablation in Transgenic Mice," *Mol. Biol. Med.* 6:523–530 (1989).
Bignami et al., "Localization of the Glial Fibrillary Acidic Protein in Astrocytes by Immunofluorescence," *Brain Res.* 43:429–435 (1972).
Bigner et al., "Patterns of the Early, Gross Chromosomal Changes in Malignant Human Gliomas," *Hereditas* 101:103–113 (1984).
Bigner et al., "Specific Chromosomal Abnormalities in Malignant Human Gliomas," *Cancer Res.* 88:405–411 (Jan. 11, 1988).
Borrelli et al., "Targeting of an Inducible Toxic Phenotype in Animal Cells," *PNAS USA* 85:7572–7576 (Oct. 1988).
Borrelli et al., "Transgenic Mice with Inducible Dwarfism," *Nature* 339:538–541 (Jun. 15, 1989).
Breakefield, X.O. and Geller, A.I., "Gene Transfer into the Nervous System," *Molec. Neurobiol.* 1:339–371 (1987).
Burdick et al., "Vitiligo in a Case of Vaccinia Virus–Treated Melanoma," *Cancer* 17(6): 708–712 (Jun. 1964).
Burger et al., "Computerized Tomographic and Pathologic Studies of the Untreated, Quiescent, and Recurrent Glioblastoma Multiforme," *J. Neurosurg.* 58:159–169 (1983).
Burk et al., "Tissue Preferential Expression of the Hepatitis B Virus (HBV) Surface Antigen Gene in Two Lines of HBV Transgenic Mice," *J. of Virology* 62(2):649–654 (1988).
Capecchi, M.R., "The New Mouse Genetics: Altering the Genome by Gene Targeting," *TIG* 5(3):70–76 (1989).
Caruso et al., "Regression of Established Macroscopic Liver Metastases After In Situ Transduction of a Suicide Gene," *PNAS USA* 90:7024–7028 (1993).
Cassel, William A., "Multiplication of Influenza Virus in the Ehrlich Ascites Carcinoma," *Cancer Research*:618–622 (1957).
Cassel et al., "A Phase II Study on the Postsurgical Management of Stage II Malignant Melanoma with a Newcastle Disease Virus Oncolysate," *Cancer* 52:856–860 (1983).
Cassel et al., "Newcastle Disease Virus as an Antineoplastic Agent," *Cancer* 18(7):863–868 (1965).

(List continued on next page.)

Primary Examiner—Deborah Crouch
(74) Attorney, Agent, or Firm—Sterne, Kessler, Goldstein & Fox P.L.L.C.

(57) ABSTRACT

The present invention discloses compositions and methods for selective killing neoplastic cells. Retroviral vectors are used to selectively express a gene in neoplastic cells. The gene or gene product targets the cells for selective killing.

9 Claims, 13 Drawing Sheets-

OTHER PUBLICATIONS

Cepko, C., "Lineage Analysis and Immortalization of Neural Cells via Retrovirus Vectors," in: Neuromethods, vol. 16, Molecular Neurobiological Techniques, Bolton et al., eds., Clifton, NJ, Humana, pp. 177–218 (1989).

Cheng et al., "Photoradiation Therapy: Current Status and Applications in the Treatment of Brain Tumors," *Surg. Neurol. 25:*423–435 (1986).

Chou et al., "Mapping of Herpes Simples Virus–1 Neurovirulence to $\gamma_1 34.5$, a Gene Nonessential for Growth in Culture," *Science 250:*1262–1266 (Nov. 30, 1990).

Coen et al., "A Genetic Approach to Promoter Recognition During trans Induction of Viral Gene Expression," *Science 234:*53–59 (Oct. 3, 1986).

Coen et al., "Thymidine Kinase–Negative Herpes Simplex Virus Mutants Establish Latency in Mouse Trigeminal Ganglia but do not Reactivate," *PNAS USA 86:*4736–4740 (Jun. 1989).

Corey et al., "Infections With Herpes Simplex Viruses, Part I," *New Engl. J. Med. 314*(11):686–691 (Mar. 13, 1986).

Corey et al., "Infections With Herpes Simplex Viruses, Part II," *New Engl. J. Med. 314*(12):749–757 (1986).

Culver et al., "In Vivo Gene Transfer with Retroviral Vector–Producer Cells for Treatment of Experimental Brain Tumors," *Science 256:*1550–1552 (Jun. 12, 1992).

Danos, O. and Mulligan, R.C., "Safe and Efficient Generation of Recombinant Retroviruses with Amphotropic and Ecotropic Host Ranges," *PNAS USA 85:*6460–6464 (Sep. 1988).

El–Azouzi et al., "Loss of Distinct Regions on the Short Arm of Chromosome 17 Associated with Tumorigenesis of Human Astrocytomas," *PNAS USA 86:*7186–7190 (Sep. 1989).

Ezzedine et al., "Selective Killing of Glioma Cells in Culture and in Vivo by Retrovirus Transfer of the Herpes Simplex Virus Thymidine Kinase Gene," *The New Biologist 3*(6):608–614 (Jun. 1991).

Ezzedine et al., "Selective Killing of Rat C6 Glioma Cells Following Retrovirus–Mediated Transfer of the Herpes Simplex Virus Thymidine Kinase Gene," *Soc. Neurosci. Abstr. 16:*Part 1, Abstract 189.3 (1990).

Field, A.K. "9–{[2–Hydroxy–1–(hydroxymethyl) ethoxy] methyl} guanine: A Selective Inhibitor of Herpes Group Virus Replication," *PNAS USA 80:*4139–4143 (Jul. 1983).

Frederiksen et al., "Immortalization of Precursor Cells from the Mammalian CNS," *Neuron 1:*439–448 (Aug. 1988).

Friedman et al., "Experimental Chemotherapy of Human Medulloblastoma Cell Lines and Transplantable Xenografts with Bifunctional Alkylating Agents," *Cancer Res. 48:*4189–4195 (Aug. 1, 1988).

Friedmann, T., "Progress Toward Human Gene Therapy," *Science 244:*1275–1281 (Jun. 16, 1988).

Fukui et al., "Detection of a raf–Related and Two Other Transforming DNA Sequences in Human Tumors Maintained in Nude Mice," *PNAS USA 82:*5954–5958 (Sep. 1985).

Gage et al., "Grafting Genetically Modified Cells to the Brain: Possibilities for the Future," *Neuroscience 23*(1):795–807 (1987).

Gannon, V.P.J., "Molecular Cloning and Nucleotide Sequence of Another Variant of the *Escherichia coli* Shiga–like Toxin II Family," *J. General Microbiol. 136:*1125–1135 (1990).

Gansbacher et al., "Retroviral Vector–mediated γ–Interferon Gene Transfer into Tumor Cells Generates Potent and Long Lasting Antitumor Immunity," *Cancer Res. 50:*7820–7825 (Dec. 15, 1990).

Geller, A.I., "A New Method to Propagate Defective HSV–1 Vectors," *Nucl. Acids Res. 16*(12):5690 (1988).

Geller, A.I. and Breakefield, X.O., "A Defective HSV–1 Vector Expresses *Escherichia coli* β–Galactosidase in Cultured Peripheral Neurons," *Science 241:*1667–1669 (Sep. 23, 1988).

Geller, A.I. and Freese, A., "Infection of Cultured Central Nervous System Neurons with a Defective Herpes Simplex Virus 1 Vector Results in Stable Expression of *Escherichia coli* β–Galactosidase," *PNAS USA 87:*1149–1153 (Feb. 1990).

Gilboa, E., "Retrovirus Vectors and Their Uses in Molecular Biology," *BioEssays 5*(6):252–257 (1987).

Glatstein et al., "The Imaging Revolution and Radiation Oncology: Use of CT, Ultrasound, and NMR for Localization, Treatment Planning and Treatment Delivery," *Intl. J. Radiation Oncology Biol. Phys. 11*(2):299–314 (Feb. 1985).

Gray et al., "Radial Arrangement of Clonally Related Cells in the Chicken Optic Tectum: Lineage Analysis with a Recombinant Retrovirus," *PNAS USA 85:*85:7356–7360 (Oct. 1988).

Gutin et al., "Recurrent Malignant Gliomas: Survival Following Interstitial Brachytherapy with High–Activity Iodine–125 Sources," *J. Neurosurg. 67:*864–873 (Dec. 1987).

Hanada et al., "Combined Effects of Acyclovir and Human Interferon–α on Herpes Simplex Virus Replication in Cultured Neural Cells," *J. Med. Virol. 29:*7–12 (1989).

Hatton, J.D., "Migration of Grafted Neonatal Astrocytes in Neonatal and Adult Hosts," *Transplantation III:,*Abstract No. 539.8 (1989).

Heimbrook et al., "Transforming Growth Factor α–Pseudomonas Exotoxin Fusion Protein Prolongs Survival of Nude Mice Bearing Tumor Xenografts," *PNAS USA 87:*4697–4701 (Jun. 1990).

Horellou et al., "Retroviral Transfer of a Human Tyrosine Hydroxylase cDNA in Various Cell Lines: Regulated Release of Dopamine in Mouse Anterior Pituitary AtT–20 Cells," *PNAS USA 86:*7233–7237 (Sep. 1989).

Huang et al., "Suppression of the Neoplastic Phenotype by Replacement of the RB Gene in Human Cancer Cells," *Science 242:*1563–1566 (Dec. 16, 1988).

Huber et al., "Retroviral–Mediated Gene Therapy for the Treatment of Hepatocellular Carcinoma: An Innovative Approach for Cancer Therapy," *Proc. Natl. Acad. Sci. USA 88:*8039–8043 (Sep. 1991).

Ito et al., "Cloning and Nucleotide Sequencing of Vero Toxin 2 Variant Genes from *Escherichia coli* 091: H21 Isolated from a Patient with the Hemolytic Uremic Syndrome," *Microbial Pathogen. 8:*47–60 (1990).

Izant, J.G. and Weintraub, H., "Constitutive and Conditional Suppression of Exogenous and Endogenous Genes by Anti–Sense RNA," *Science 229:*345–352 (Jul. 26, 1985).

Jacque et al., "Interspecies Identification of Astrocytes after Intracerebral Transplantation," *Dev. Neurosci. 8:*142–149 (1986).

James et al., "Clonal Genomic Alterations in Glioma Malignancy Stages," *Cancer Res. 48:*5546–5551 (Oct. 1, 1988).

Kabat, D., "Molecular Biology of Friend Viral Erythroleukemia," *Curr. Topics in Microbiol. and Immunol. 148:*1–41 (1989).

Kasid et al., "Effect of Antisense c–raf–1 on Tumorigenicity and Radiation Sensitivity of a Human Squamous Carcinoma" *Science 243:*1354–1356 (Mar. 10, 1989).

Kay et al., "Retrovirus–Induced Spongiform Myeloencephalopathy in Mice: Regional Distribution of Infected Target Cells and Neuronal Loss Occurring in the Absence of Viral Expression in Neurons," *PNAS USA 88:*1281–1285 (Feb. 1991).

Kim, S.K. and Wold, B.J., "Stable Reduction of Thymidine Kinase Activity in Cells Expressing High Levels of Anti–Sense RNA," *Cell 42:*129–138 (Aug. 1985).

Kim et al., "Correlates of Survival and the Daumas–Duport Grading System for Astrocytomas," *J. Neurosurg. 74:*27–37 (Jan. 1991).

Kobayashi, H., "Viral Xenogenization of Intact Tumor Cells," *Advances in Cancer Res. 30:*279–299 (1979).

Le Doussal et al., "Targeting of Indium 111–Labeled Bivalent Hapten to Human Melanoma Mediated by Bispecific Monoclonal Antibody Conjugates: Imaging of Tumors Hosted in Nude Mice," *Cancer Res. 50:*3445–3452 (Jun. 1, 1990).

Lendahl et al., "CNS Stem Cells Express a New Class of Intermediate Filament Protein," *Cell 60:*585–595 (Feb. 23, 1990).

Luskin et al., "Cell Lineage in the Cerebral Cortex of the Mouse Studied In Vivo and In Vitro With a Recombinant Retrovirus," *Neuron 1:*635–647 (Oct. 1988).

Macchi et al., "Effect of Human T Lymphotropic Retrovirus–I Exposure on Cultured Human Glioma Cell Lines," *Acta Neuropathol. 81:*670–674 (1991).

Mahaley et al., "National Survey of Patterns of Care for Brain–Tumor Patients," *J. Neurosurg. 71:*826–836 (1989).

Mann et al., "Construction of a Retrovirus Packaging Mutant and Its Use to Produce Helper–Free Defective Retrovirus," *Cell 33:*153–159 (May 1983).

Martuza et al., "Experimental Therapy of Human Glioma by Means of a Genetically Engineered Virus Mutant," *Science 252:*854–856 (May 10, 1991).

Matz et al., "Physical Mapping of Temperature–sensitive Mutations of Herpes Simplex Virus Type 1 Using Cloned Restriction Endonculease Fragments," *J. gen. Virol. 64:*2261–2270 (1983).

McGarry, T.J. and Lindquist, S., "Inhibition of Heat Shock Protein Synthesis by Heat–Inducible Antisense RNA," *PNAS USA 83:*399–403 (Jan. 1986).

McKnight, S.L., "The Nucleotide Sequence and Transcript Map of the Herpes Simplex Virus Thymidine Kinase Gene," *Nucl. Acids Res. 8*(24):5949–5964 (1980).

McLaren et al., "Preclinical Investigations of FIAU, an Anti–Herpes Agent," *Herpes Viruses and Virus Chemotherapy,* pp. 57–61 (1985).

Melton, D.A., "Injected Anti–Sense RNAs Specifically Block Messenger RNA Translation In Vivo," *PNAS USA 82:*144–148 (Jan. 1985).

Miller, A.D. and Buttimore, C., "Redesign of Retrovirus Packaging Cell Lines To Avoid Recombination Leading to Helper Virus Production," *Molec. Cell. Biol. 6*(8):2895–2902 (Aug. 1986).

Miyanohara et al., "Expression of Hepatitis B Surface Antigen Gene in Yeast," *PNAS USA 80:*1–5 (Jan. 1983).

Moolten, F.L., "Tumor Chemosensitivity Conferred by Inserted Herpes Thymidine Kinase Genes: Paradigm for a Prospective Cancer Control Strategy," *Cancer Res. 46:*5276–5281 (Oct. 1986).

Moolten, F.L. and Wells, J.M., "Curability of Tumors Bearing Herpes Thymidine Kinase Genes Transferred by Retroviral Vectors," *J. Natl. Cancer Inst. 82*(4):297–300 (Feb. 21, 1990).

Moolten et al., "Lymphoma Regression Induced by Ganciclovir in Mice Bearing a Herpes Thymidine Kinase Transgene," *Human Gene Ther. 1:*125–134 (1990).

Moore, A.E., "The Oncolytic Viruses," *Progr. exp. Tumor Res. 1:*411–439 (1960).

Nagashima, T. and Hoshino, T., "Rapid Detection of S–Phase Cells by Anti–bromodeoxyuridine Monoclonal Antibody in 9L Brain Tumor Cells In Vitro and In Situ," *Acta Neuropathol. 66:*12–17 (1985).

Oldfield et al., "Clinical Protocols—Gene Therapy for the Treatment of Brain Tumors Using Intra–Tumoral Transduction with the Thymidine Kinase Gene and Intravenous Ganciclovir," *Human Gene Ther. 4:*39–69 (1993).

Palabrica et al., "Thrombus Imaging in a Primate Model with Antibodies Specific for an External Membrane Protein of Activated Platelets," *PNAS USA 86:*1036–1040 (Feb. 1989).

Palella et al., "Herpes Simplex Virus–Mediated Human Hypoxanthin–Guanine Phosphoribosyltransferase Gene Transfer into Neuronal Cells," *Molec. Cell. Biol. 8*(1):457–460 (Jan. 1988).

Plautz et al., "Selective Elimination of Recombinat Genes in Vivo With a Suicide Retroviral Vector," *The New Biologist 3*(7):709–715 (Jul. 1991).

Preiss et al., "Molecular Genetics of Krüppel, a Gene Required for Segmentation of the Drosophila Embryo," *Nature 313:*27–32 (Jan. 3, 1985).

Price et al., "Lineage Analysis in the Vertebrate Nervous System by Retrovirus–Mediated Gene Transfer," *PNAS USA 84:*156–160 (Jan. 1987).

Ram et al., "In Situ Retroviral–mediated Gene Transfer for the Treatment of Brain Tumors in Rats," *Cancer Res. 53:*83–88 (Jan. 1, 1993).

Raney et al., "Characterization of Hepatitis B Virus Major Surface Antigen Gene Transcriptional Regulatory Elements in Differentiated Hepatoma Cell Lines," *J. Virol. 63*(9):3919–3925 (Sep. 1989).

Roenigk, H.H. and Deodhar, S., "Immunotherapy of Malignant Melanoma With Vaccinia Virus," *Arch. Dermatol. 109:*668–673 (May 1974).

Rosenberg, S.A., "Immunotherapy and Gene Therapy of Cancer," *Cancer Res. (Suppl.) 51:*5074s–5079s (Sep. 15, 1991).

Rosenberg et al., "Grafting Genetically Modified Cells to the Damaged Brain: Restorative Effects of NGF Expression," *Science 242:*1575–1578 (Dec. 16, 1988).

Rosenberg et al., "Production of Phenocopies by Krüppel Antisense RNA Injection into Drosophila Embryos," *Nature 313:*703–706 (Feb. 21, 1985).

Ryder et al., "Establishment and Characterization of Multipotent Neural Cell Lines Using Retrovirus Vector–Mediated Oncogene Transfer," *J. Neurobiol. 21*(2):356–375 (1990).

Salcman, M. and Samaras, G.M., "Interstitial Microwave Hyperthermia for Brain Tumors," *J. Neuro–Oncol. 1:*225–236 (1983).

Sealy et al., "Interstitial Misonidazole—A Preliminary Report on a New Perspective in Clinical Radiation Sensitization and Hypoxic Cell Chemotherapy," *Cancer* 54:1535–1540 (1984).

Sharpe et al., "Role of Abortive Retroviral Infection of Neurons in Spongiform CNS Degeneration," *Nature* 346:181–183 (Jul. 12, 1990).

Shih et al., "Herpes Simplex Virus as a Vector for Eukaryotic Viral Genes," *Vaccines* 85:177–180 (1985).

Shimohama et al., "Grafting Genetically Modified Cells into the Rat Brain: Characteristics of *E. coli* β–Galactosidase as a Reporter Gene," *Molec. Brain Res.* 5:271–278 (1989).

Short et al., "Autocrine Differentiation of PC12 Cells Mediated by Retroviral Vectors," *Dev. Neurosci.* 12:34–45 (1990).

Short et al., "Direct Infection of Rat C6 Glioma Cells in the Brain by Grafting of a Retrovirus Packaging Line," *Soc. for Neurosci. Abstr.* 16:449 Part 1, Abstract 189.2 (1990).

Short et al., "Gene Delivery to Glioma Cells in Rat Brain by Grafting of a Retrovirus Packaging Cell Line," *J. Neurosci. Res.* 27:427–433 (1990).

Smiley, James R., "Construction In Vitro and Rescue of a Thymidine Kinase–Deficient Deletion Mutation of Herpes Simplex Virus," *Nature* 285:333–335 (May 29, 1980).

Snyderman et al., "Cisplatin Sensitization to Radiotherapy in Stage IV Squamous Cell Carcinoma of the Head and Neck," *Arch. Otolaryngol. Head Neck Surg.* 112:1147–1150 (Nov. 1986).

Takamiya et al., "An Experimental Model of Retrovirus Gene Therapy for Malignant Brain Tumors," *J. Neurosurg.* 79:104–110 (1993).

Takamiya et al., "Gene Therapy of Malignant Brain Tumors: A Rat Glioma Line Bearing the Herpes Simplex Virus Type 1–Thymidine Kinase Gene and Wild–Type Retrovirus Kills Other Tumor Cells," *J. Neurosci. Res.* 33:493–503 (1992).

Takátsy et al., "Virus in Human Cancer Cells in Vivo," *Virology* 5:395–400 (1958).

Takle et al., "Cloning and Expression of a Trypomastigote–Specific 85 Kilodalton Surface Antigen Gene from *Trypanosoma cruzi*," *Molec. Biochem. Parasitol.* 37:57–64 (1989).

Thompson, R.L. and Stevens, J.G., "Biological Characterization of a Herpes Simplex Virus Intertypic Recombinant which is Completely and Specifically Non–Neurovirulent," *Virology* 131:171–179 (1983).*

Thompson et al., "Herpes Simplex Virus Neurovirulence and Productive Infection of Neural Cells Is Associated with a Function Which Maps between 0.82 and 0.832 Map Units on the HSV Genome," *Virology* 172:435–450 (1989).*

Tondravi, M.M., "DNA Rearrangements Associated with the H3 Surface Antigen Gene of *Tetrahymena thermophila* that Occur During Macronuclear Development," *Curr. Genet.* 14:617–626 (1988).*

Turner, D.L. and Cepko, C.L., "A Common Progenitor for Neurons and Glia Persists in Rat Retina Late in Development," *Nature* 328:131–136 (Jul. 9, 1987).

Walsh, C. and Cepko, C.L., "Clonally Related Cortical Cells Show Several Migration Patterns," *Science* 241:1342–1345 (Sep. 9, 1988).

Welt et al., "Monoclonal Antibody to an Intracellular Antigen Images Human Melanoma Transplants in nu/nu Mice," *PNAS USA* 84:4200–4204 (Jun. 1987).

West, S.C. and Howard–Flanders, P., "Duplex–Duplex Interactions Catalyzed by RecA Protein Allow Strand Exchanges to Pass Double–Strand Breaks in DNA," *Cell* 37:683–691 (Jun. 1984).

Wolf et al., "Retrovirus–Mediated Gene Transfer of Beta–nerve Growth Factor into Mouse Pituitary Line AtT–20," *Molec. Biol. Med.* 5:43–59 (1988).

Wolff et al., "Grafting Fibroblasts Genetically Modified to Produce L–Dopa in a Rat Model of Parkinson Disease," *PNAS USA* 86:9011–9014 (Nov. 1989).

Wowra et al., "Incidence of Late Radiation Necrosis with Transient Mass Effect After Interstitial Low Dose Rate Radiotherapy for Cerebral Gliomas," Acta Neurochirurgica 99:104–108 (1989).

Yoshii et al., "Estimation of Growth Fraction with Bromodeoxyuridine in Human Central Nervous System Tumors," *J. Neurosurg.* 65:659–663 (1986).

Zamorano et al., "Tumor Recurrence vs. Radionecrosis: an Indication for Multitrajector Serial Sterotactic Biopsies," *Acta Neurochirurgica Suppl.* 46:90–93 (1989).

Zhou et al., "Timing and Patterns of Astrocyte Migration From Xenogeneic Transplants of the Cortex and Corpus Callosum," *J. Compar. Neurol.* 292:320–330 (1990).

* cited by examiner

IMPLANTING HSV-TK RETROVIRUS PRODUCING CELLS TO TREAT TUMORS

This application is a continuation division of application Ser. No. 07/895,364, filed Jun. 9, 1992, which is a continuation-in-part of application Ser. No. 07/746,655, filed Aug. 16, 1991, abandoned, which is a continuation-in-part of application Ser. No. 07/582,055, filed Sep. 14, 1990, abandoned.

The present invention was made using funds of the United States Government. The U.S. government is granted a royalty-free, non-exclusive, worldwide and paid-up license to this invention.

FIELD OF THE INVENTION

This invention relates to treatment of neoplastic cells utilizing viruses and viral vectors.

BACKGROUND OF THE INVENTION

Neoplasia is a process by which the normal controlling mechanisms that regulate cell growth and differentiation are impaired resulting in progressive growth. During neoplasia, there is a characteristic failure to control cell turnover and growth. This lack of control causes a tumor to grow progressively, enlarging and occupying spaces in vital areas of the body. If the tumor invades surrounding tissue and is transported to distant sites the tendency of this tumor will be to result in death of the individual.

One-third of all individuals in the United States will develop cancer (American Cancer Society Yearly Outlook for 1990). The five year survival rate for these patients has risen to nearly 50% as a result of progress and early diagnosis and therapy of the disease (American Cancer Society Yearly Outlook for 1990). However, cancer remains second only to cardiac disease as a cause of death in this country (American Cancer Society Yearly Outlook for 1990). Nearly 20% of all Americans who die this year will die of cancer (American Cancer Society Yearly Outlook for 1990). Half of these deaths will be-due to the three most common types of cancer: lung, breast, and colon.

Recently there has been a rapid expansion of cancer treatments. Even though new treatments are being developed, the need still exists for improved methods for the treatment of most types of cancers.

The preferential killing of cancer cells without deleterious effect on normal cells is the desired goal in cancer therapy. In the past this has been accomplished using a variety of procedures. These procedures include the administration of chemicals, chemotherapy, radiation, radiotherapy, and surgery.

Radiotherapy is a regional form of treatment used for the control of localized cancers (See Devita, V. T., in Harrison's Principles of Internal Medicine, ed. Braunwald et al., 1987, McGraw-Hill Inc., New York, p. 431–446). Radiotherapy relies on the fact that some malignant diseases are more susceptible to damage by radiation. This difference in susceptibility depends on normal cells having a higher capacity for intercellular repair than neoplastic cells and the ability of normal organs to continue to function well if they are only segmentally damaged. If surrounding tissue can tolerate twice the radiation dose of a given tumor, then the tumor is radiosensitive. On the other hand, some tumors cannot be treated with radiotherapy. Cancer which extensively involves both lungs cannot be treated effectively with radiation therapy because of the greater radiosensitivity of the surrounding- lung tissue (See Devita, V. T., in Harrison's Principles of Internal Medicine, ed. Braunwald et al., 1987, McGraw-Hill Inc., New York, p. 431–446).

Surgery is still considered the primary treatment for most early cancers (See Devita, V. T., in Harrison's Principles of Internal Medicine, ed. Braunwald et al., 1987, McGraw-Hill Inc., New York, p. 431–446). However, most tumors are operable but not fully resectable. Some tumors that appear resectable have micrometastatic disease outside the tumor field. This leads to a recurrence of the cancer close to the initial site of occurrence. Any cancer showing a level of metastasis effectively cannot be cured through surgery.

Other types of localized therapy (nonsystemic) have been explored. These include local hyperthermia (Salcman et al., J. Neuro-Oncol. 1:225–236 (1983)), photodynamic therapy (Cheng et al., Surg. Neurol. 25:423–435 (1986)), and interstitial radiation (Gutin et al., J. Neurosurgery 67:864–873 (1987)). To date these therapies have been met with limited success.

Radiotherapy and surgery offers ways of reducing the tumor mass in specific regions of the body that are accessible through surgical techniques or high doses of radiotherapy. Neither is applicable to the destruction of widely disseminated or circulating tumor cells characteristically present in most patients with cancer. This is the stimulus of the development of systemic treatments of cancer such as chemotherapy.

The use of chemicals, even though widespread in use, has proved limitedly effective in treating most cancer types. One drawback to the use of cytotoxic agents for the treatment of cancer are their severe side effects. These include nausea, vomiting, CNS depression, localized pain, bone marrow depression, bleeding, renal damage, hypo and hyperglycemia and hypersensitivity reactions. Another drawback is that they are only effective against rapidly dividing cells.

A more modern approach to chemotherapy is to direct the toxic agents to the cancer cells themselves. This has been accomplished experimentally by linking the chemotherapeutic agent to either antibodies or toxic molecules that have a higher affinity for the tumor cells than normal cells. These directed toxic bullets are still in an early clinical phase of development and are not commercially available.

Certain types of cancer, for example gliomas, which are the most common primary tumor arising in the human brain, defy the current modalities of treatment. Despite surgery, chemotherapy, and radiotherapy, glioblastoma multifoime, the most common of the gliomas is almost universally fatal (Schoenberg, B. S., "The epidemiology of nervous system tumors," in Oncology of the Nervous System, M. D. Walker, ed., Boston, Mass., Martinus Nijhoff (1983); Levin et al., "Neoplasms of the Central Nervous System," Chapter 46, pp. 1557–1611, in Cancer: Principles and Practice of Oncology, vol. 2, 3rd ed., De Vita et al., eds., Philadelphia, Lippincott Press (1989)).

Gliomas represent nearly 40% of all primary brain tumors, with glioblastoma multiforme constituting the most malignant form (Schoenberg, B. S., "The epidemiology of nervous system tumors," in Oncology of the Nervous System, Walker, M. D., ed., Cold Spring Harbor Lboratory, Cold Spring Harbor, N.Y. (1983)). The five year survival rate for persons with this high grade type of astrocytoma is less than 5 percent given current treatment modalities of surgery, radiation therapy and/or chemotherapy (Mahaley et al., Neurosurgery 71:826–836 (1989); Schoenberg, B. S., "The epidemiology of nervous system tumors," in Oncology of the Nervous System, Walker, M. D., ed., Cold Spring Harbor Laboratory, Cold Spring Harbor, N.Y. (1983); Kim et al., J.

*Neurosurg.* 74:27–37 (1991), Daumas-Duport et al., *Cancer* 62:2152–2165 (1988)).

The resistance of glioblastomas to current chemotherapy may reflect the proliferative characteristics of this tumor type which are in-between lower grades of astrocytoma and other types of metastatic tumors in the central nervous system (CNS), (Nagashima and Hoshino, *Acta Neuropathol.* 66:12–17 (1985)). The bromodeoxyuridine labelling index, which measures the percentage of cells which are in S phase at any given moment, is 7.3% in glioblastoma tumors, which is 2 to 7 times higher than in lower grade astrocytomas, but less than in metastatic tumors (Nagashima and Hoshino, supra).

A related parameter that is useful for appreciating the relative resistance of glioblastomas to current therapeutic modalities is the growth fraction, or the relative proportion of cells proliferating in the tumor at any one time. The growth fraction in this tumor type is only 30%, with the remaining 70% of cells being in $G_o$, a resting phase (cells in $G_o$ may die or may re-enter the active cell cycle; Yoshii et al., *J. Neurosurg.* 65:659–663 (1986)), while the 30% of glioblastoma cells that are actively dividing contribute to the lethal progression of this tumor, the 70% that are quiescent are responsible for the resistance of these tumors to a number of chemotherapeutic agents that target actively proliferating cells.

Further, surgical modalities for glioblastomas are hampered by the lack of distinct boundaries between the tumor and the surrounding parenchyma, and by the migration of tumor cells in the white matter tracts extending out from the primary site (Burger et al., *J. Neurosurg.* 58:159–169 (1983)), which preclude their complete removal.

Radiation therapy has also had limited success due to the low growth fraction in these tumors as well as to the radiation sensitivity of adjacent normal tissue (Wowra et al., *Acta Neurochir.* (Wien) 99:104–108 (1983); Zamorano et al., *Acta Neurochir. Suppl.* (Wien) 46:90–93 (1989)).

New approaches are needed to treat brain tumors. The herpes simplex virus type 1 (HSV) thymidine kinase (TK) gene has been introduced into retrovirus vectors to transfer conditional sensitivity to nucleoside analogues, such as ganciclovir, to lymphoma, sarcoma and murine adenocarcinoma cells in culture and in vivo (Moolten, F. L., *Cancer Res.* 46:5276–5281 (1986); Moolten, F. L., et al., *Human Gene Ther.* 1:125–134 (1990); Plautz, G., et al., *New Biol.* 3:709–715 (1991); Moolten and Wells, *J. Natl. Cancer Inst.* 82:297–300 (1990)). Ganciclovir is a guanosine analogue that is specifically converted by HSV-TK to an intermediate capable of inhibiting DNA synthesis (Field, A. K., et al., *Proc. Natl. Acad. Sci. USA* 80:4139–4143 (1983)). Ezzedine et al. (*New Biol.* 3:608–614 (1991)) used a similar retrovirus vector, VIK, to transfer chemosensitivity to rat C6glioma cells in culture and in vivo. The HSV-TK gene has also been used to mediate conditional toxicity in a number of other models, including cellular ablations in transgenic mice (Bernstein and Breitman, *Mol. Biol. Med.* 6:523–530 (1983); Borrelli et al., *Proc. Natl. Acad. Sci. USA* 85:7572–7576 (1988); Borrelli et al., *Nature* 339:538–541 (1989); Heyman et al., *Proc. N., Proc. Natl. Acad. Sci. USA* 86:2698–2702 (1989)).

Therefore a need exists for the development of a technique that will selectively destroy glioma while sparing normal brain cells. The present methods can be used universally for the selective destruction of all types of neoplastic cells.

SUMMARY OF THE INVENTION

Compositions and methods are provided for selectively killing neoplastic cells. In particular, retroviral vectors are utilized to target expression of a gene or gene product in neoplastic cells. Genes are selected whose gene products are capable of targeting cells for selective killing of tumor cells. The methods find particular use in the treatment of tumors of the nervous system.

The present inventors have discovered that retroviral vectors represent a novel strategy to deliver foreign genes with biological consequences to tumor cells.

DETAILED DESCRIPTION OF THE INVENTION

Figure 1:
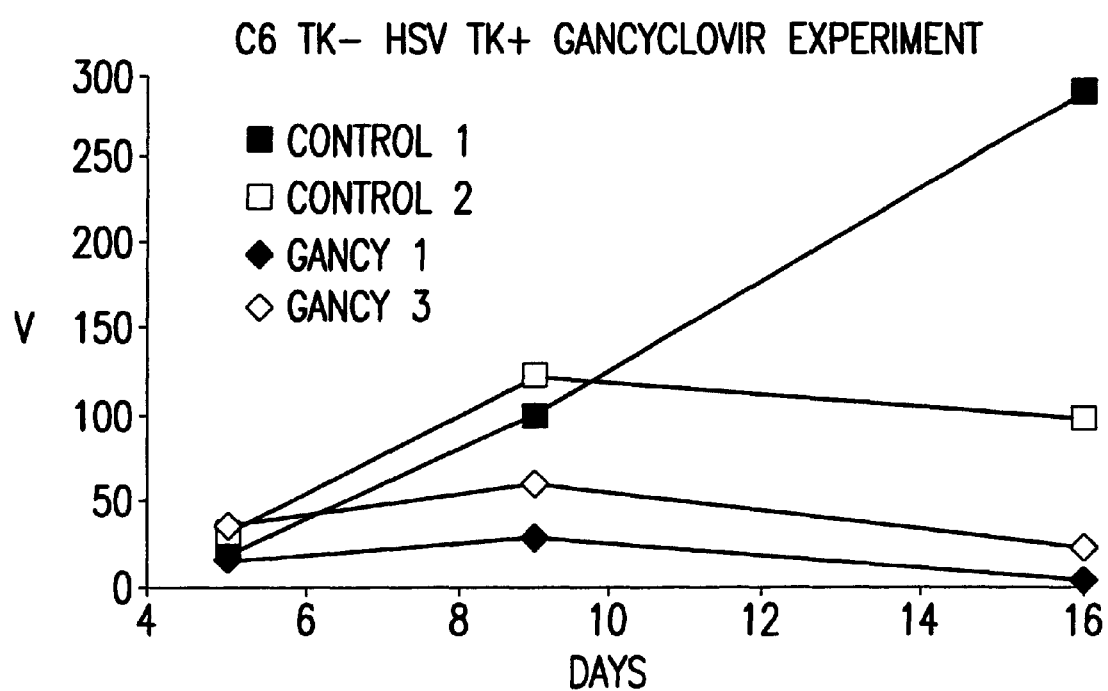
FIG. 1: Graph of in vivo study of ganciclovir.
Figure 2:
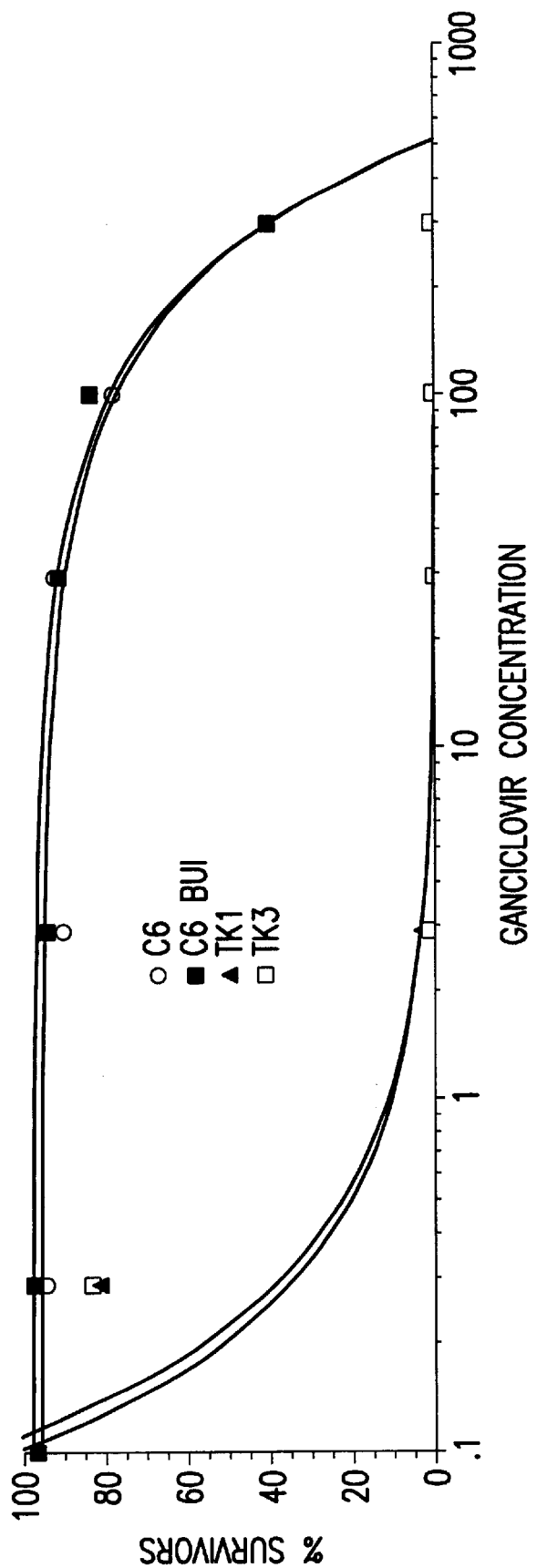
FIG. 2: Graph of the ganciclovir sensitivity assay.

The present invention is drawn to the selective killing of neoplastic cells. Retrovirus vectors carrying a gene whose gene product is capable of targeting the neoplastic cells for selective cell death are utilized.

By neoplastic cells is intended dividing cells, usually rapidly dividing cells. For purposes of the invention, neoplastic cells include cells of tumors, neoplasms, carcinomas, sarcomas, leukemias, lymphomas, and the like. Of particular interest are central nervous system tumors. These include astrocytomas, oligodendrogliomas, meningiomas, neurofibromas, ependymomas, Schwannomas, neurofibrosarcomas, glioblastomas, etc. The neoplastic cells of particular concern to the invention are those cells of brain tumors. Adult brain tumors are unique in that they constitute masses of dividing cells within a background of essentially non-dividing cells. Therefore, the present invention utilizes these metabolic differences to exploit the development of a targeted approach to selective killing of neoplastic cells. The invention can be utilized to selectively kill both benign and malignant neoplastic cells.

The retroviral vectors of the invention can integrate only into the genome of dividing cells. Thus, the vectors provide a useful vehicle for selective targeting of dividing cells. Retroviral vectors offer further advantages as there are no limitations in host range and these vectors have already been used successfully to infect many different cell types. For example, see Cepko, C., "Lineage analysis and immortalization of neural cells via retrovirus vectors," in Neuromethods, Vol. 16,pp. 177–218, Clifton, N.J., The Humana Press, Inc. (1989); Gilboa, E., BioEssays 5(6) :252–257 (1987); Friedmann, T., Science 244:1275–1281(1989).

In genemeral, retroviral vectors are well known in the art. See, Breakefield et, al., Molec. Neuro. Biol. 1:339 (1987); and, Shih et al., In: Vaccines 85, Cold Spring Harbor Press, Cold Spring Harbor, N.Y. (1985) pages 177–180. Further, co-pending U.S. patent applications Ser. Nos. 07/304,619 and 07/508,731 are drawn to herpes simplex virus expression vectors. The disclosures, of these applications are herein incorporated by reference. These applications provide further information on the construction and use of retrovirus vectors.

As indicated above, generally, the retrovirus vectors of, the present invention are replication-defective and can be packaged into infectious retroviral, particles by transfected, cell lines which contain retroviral sequences coding for the proteins necessary for the packaging of retroviral RNA, but which cannot package their own RNA. See, Mann et al., Cell 33:153-159 (1983); Danos and Mulligan, Proc. Natl. Acad. Sci. USA 85:6460–6464 (1988). Since retrovirus and vectors derived from them integrate into the host cell genome, their sequences are transmitted to all daughter cells. This feature of retroviruses has been successfully used for example, to trace cell lineages in the nervous system (Price et al., Proc. Natl. Acad. Sci. USA 84:156–160 (1987); Luskin et al., Neuron 1:635–647 (1988); Walsh and Cepko, Science 241:1342–1345(1988)).

Genes for transfer into the neoplastic cells by the retroviral vectors are selected from those which target the host cell usually by the expression of a gene product in the host neoplastic cells. "Gene product" broadly refers to proteins encoded by the particular gene. However, for purposes of the invention, gene product also includes transcription products of the gene, particularly for use as anti-sense RNA. The host cells targeted by the present vectors are those cells into which the virus infects and expresses the desired gene product. The host cells thus constitute neoplastic cells infected by the retroviral vectors.

Genes are selected whose gene products serve to identify host cells, slow down or temporarily stimulate host cell growth in order to render the host cell more sensitive to chemotherapeutic agents and/or whose products target the host cell for cell death. Cell death can be accomplished by contacting the host cells, comprising the gene product, with a subsequent treatment, either physical or chemical treatment. Alternatively, the gene products themselves may serve to kill the host cells or slow down cell growth. Gene products which temporarily stimulate cell growth include for example, growth factors, including for example basic fibroblast growth factor, (bFGF).

In this respect, one example of a useful gene product comprises imaging compounds which may be utilized for tumor location. The retrovirus is thus utilized as a means to diagnose the location and extent of the neoplastic growth. See, for example. Glatstein et al., Int. J. Radiat. Oncol. Biol. Phys. 11:299–314(1985).

Genes are also selected whose products themselves are capable of selective cell killing. For example, the gene product may comprise anti-sense nucleic acid for essential cell proteins, such as replication proteins, which serve to render the host cells incapable of further cell growth and division. Anti-sense regulation has been described by Rosenberg et al., Nature 313:703–706 (1985); Preiss at al., Nature 313:27–32(1985); Melton, Proc. Natl. Acad. Sci. USA 82:144–148 (1985); Izant and Weintraub, Science 229:345–352 (1985); Kim and Wald, Cell 42:129–138 (1985); Pestka et al., Proc. Natl. Acad. Sci. USA 81:7525-7528 (1984); Coleman at al., Cell 37:683–691

(1984); and McGarry and Lindquist, *Proc. Natl. Acad. Sci. USA* 83:399–403 (1986).

Other genes which find use for slowing cell growth include tumor suppressor genes, genes which encode transcription factors which suppress cell growth, toxic proteins that are released by cells, and the like. For example, see Heinbrook at al., *Proc. Natl. Acad. Sci. USA* 87:4697 (1990), which describes a fusion protein with toxin coupled to the EGF ligand. Toxin genes have also been described, for example, Barker at al., *Gene* 86:285–290 (1990); Ito at al., *Microb. Pathog.* 8:47–60 (1990); Gannon et al., *J. Gen. Microbiol.* 136:1125–1136 (1990). Genes can also be inserted which alter cell growth characteristics or modulate cell growth, for example, a tumor suppressor gene such as the Rb gene in retinoblastoma (Huang et al., *Science* 242:1563–1566 (1988)) or the p53 gene in colon cancer (Baker et al., *Science* 249:912–915 (1980)). Other suppressor or modulating genes may also be utilized.

Genes whose products serve to render the host cells more antigenic also find use in the invention. This antigenic effect may be accomplished by introducing new antigens on the surface of the host cells, thus augmenting the immune system in recognizing the tumor as a foreign body. The introduction of new antigens to the surface of the host cells is referred to as xenogenization of the cells (Austin et al., Ad. in *Cancer Res.* 30:301–345 (1979); Kobayashi at al., Ad. in *Cancer Res.* 30:279–299 (1979)). Any nonhuman surface antigen can be utilized including those described in Araki et al., *Gene* 89:195–202 (1990); Takle et al., *Mol. Biochem. Parasitol.* 37:57–64 (1989); Raney et al., *J. Virol.* 63:3919–3925 (1989); Tondravi, M. M., *Curr. Genet.* 14:617,–626 (1988); and Miyanhara et al., *Proc. Natl. Acad. Sci. USA* 80:1–5 (1983).

The expression of nonhuman or unique surface antigens in neoplastic cells can also be utilized to locate such neoplastic cells by subsequent binding with labelled antibodies. See, for example, Le Doussal et al., *Cancer Res.* 50:3445–3452 (1990); Palabrica at al., *Proc. Natl. Acad. Sci. USA* 86: 1036–1040 (1989); Berends et al., *Cancer Immunol. Immunother.* 26:243–249 (1988); and Welt et al., *Proc. Natl. Acad. Sci. USA* 84:4200–4204 (1987).

Alternatively, the gene or coding sequence may be selected whose Products offer a conditional killing mechanism for dividing cells. In this manner, the expression of a particular protein followed by the subsequent treatment is effective in killing the neoplastic cells. The subsequent treatment comprises chemical and physical treatments. Agents for chemical treatments comprise the use of enzymes or other compounds which react with the gene product to kill the host cell. Physical treatments comprise subjection of the cells to radiation, UV light, and the like.

For example, the herpes simplex virus type I (HSV-1), thymidine kinase (TK) gene offers such a conditional killing mechanism for dividing cells. The selective advantage of using HSV-1-TK derived from the fact that the enzyme has a higher affinity for certain nucleoside analogues, such as acyclovir, ganciclovir and FIAU, than mammalian TK (McLaren at al., In: *Herpes Virus and Virus Chemotherapy*, R. Kono, ed., pp. 57–61, Amsterdam, Elsevier (1985)). These drugs are converted to nucleotide-like precursors and incorporated into the DNA of replicating cells, thus disrupting the integrity of the genome, and ultimately leading to cell death. Several studies have successfully made use of the conditional toxicity of TK in development studies of transgenic mice (Borrelli et al., *Nature* 339:538–541 (1983); Heyman et al., *Proc. Natl. Acad. Sci. USA* 86:2698–2702 (1989)), as a selectable marker against non-homologous recombination events in cultured cells (Capecchi, M. R., *Trends in Genetics* 5 (3):70–76 (1989)), for killing cells harboring wild type herpes viruses (Corey and Spear, *N. Engl. J. Med.* 314:686–691 (1986); Corey and Spear, *N. Engl. J. Med.* 314:749–756 (1986)), and in selecting for herpes virus mutants lacking TK activity (Coen et al., *Science* 234:53–59 (1986)).

The gene product may also encode a chemical or protein which renders the host cells radiosensitive and thus more susceptible to killing by radiation. Thus, upon subsequent subjection to radiation, the host cells are selectively killed. For example, the combination of the HSV-TK gene and ganciclovir, can be used. Cells bearing the HSV-TK gene show increased sensitivity to radiation in the presence of ganciclovir, as its metabolites interfere with DNA repair as well as DNA synthesis. See Snyderman et al., Arch. OtolaryngoL *Head Neck Surg.* 112:1147–1150 (1986); and Sealy at al., *Cancer* 54:1535–1540 (1984). Other strategies include selective transfer of cell surface antigenic markers, in conjunction with the development of tumor-specific immunoconjugates to improve targeting of chemotherapeutic agents. See, Reisfeld, R. A., in *Molecular Probes Technology and Medical Applications*, Albertini at al., Raven Press, New York (1989).

It is recognized that the gene of interest may be modified by any methods known in the art. For example, the gene may be placed under the control of heterologous regulatory regions, including the use of viral promoters, neoplastic cell or tumor specific promoters or control elements. In this manner, the gene product is further targeted to specific cell types. Methods for construction of such expression vectors are known in the art.

Generally, methods are known in the art for retroviral infection of the cells of interest. Typically, the virus is injected into the host at or near the site of neoplastic growth. For the most part, the virus is provided in a therapeutically effective amount to infect and kill target cells. Generally, the virus is provided for injection in a concentration in the range of about $10^1$ to about $10^{10}$ plaque forming units (PFU), generally about $5\times10^4$ to about $1\times10^6$ PFU, more generally about $1\times10^5$ to about $4\times10^5$, although ranges may vary. Alternatively, the packaging cell line may be grafted near or into the tumor to provide a longer-lasting source of virus.

This Selective killing of the retrovirus and delivery of the toxic gene can be enhanced by co-infection with a helper virus. That is, the helper virus augments gene delivery. In this manner, the packaging cell lines for making virus particles of the retrovirus vectors can be coinfected with a helper virus. Packaging cells or viral inoculum is then injected into the host at or near the site of infection. (See, Cepko, C. (1989), supra; Rosenberg et al., *Science* 242:1575–1578 (1988); and Mann et al., *Cell* 33:153–159 (1983)). Such helper viruses include ecotrbpic wild-type retroviruses, for example MoMLV (See, Danos et al., *Proc. Natl. Acad. Sci. USA* 85:6460–6464 (1988); Cepko, C., In *Neuromethods, Vol.* 16, Molecular Neurobiological Techniques, Boulton et al. (eds.), Clifton, N.J. Humana (1983); and Mann et al., Cell 33:153–159 (1983)).

To utilize a helper virus, the packaging line or retroviral vector-infected line can be subsequently infected with wild-type virus in culture and these cells can be grafted. (See, Rosenberg at al., *Science* 242:1575–1578 (1988) and Wolff et al., *Proc. Natl. Acad. Sci. USA* 86:9011–9014 (1989)). The packaging cells are infected with the helper in the range of MOI of about 0.1 to about 20.

The sensitivity of the tumor cells to toxic agents is increased utilizing helper viruses. The helper viruses turn cells infected with retrovirus vectors into packaging cell lines. The results show that by co-infection with a helper virus, the. retrovirus vectors of the invention are able to target more tumor cells, even those tumor cells away from the tumor mass. Furthermore, the tumor cells die faster and show more sensitivity to toxic agents when a helper virus is utilized.

The invention finds particular use in the treatment of glioblastomas. Glioblastomas are the most common form of malignant brain tumor in man, and are almost always universally fatal. The glioblastoma represents approximately 30% or 50% of all primary brain tumors and, despite surgery, chemotherapy, and radiotherapy, are almost universally fatal. The mean survival is less than a year, and the five-year survival rate is only 3% or 5%. After treatment, reoccurrence of the disease often appears within two centimeters of the original site. Metastases are extremely rare; neurological disfunction and death are due to local growth and cerebral invasion. Therefore, the possible efficacy of local (non-systemic) treatments has been explored. A few of these include studies of local hypothermia, photodynamic therapy, and interstitial radiation. Until the present invention, no therapeutic modality has made a substantial impact on the outcome of patients with malignant gliomas.

The following Examples are offered by way of illustration, not by way of limitation.

Experimental

EXAMPLE 1

Primary human brain tumors (malignant gliomas) are not encapsulated, and it is therefore difficult to ensure their complete removal surgically. Many of these tumors are non-metastatic and may, at times, only invade a few centimeters into the surrounding tissue. However, surgery, radiotherapy and chemotherapy have only had a modest impact on the overall morbidity and mortality of affected individuals. Novel, targeted approaches to the treatment of malignant gliomas are worthy of exploration.

Brain tumors are unique in that they constitute masses of dividing cells within a background of essentially non-dividing cells. These metabolic differences can be exploited in the development of targeted approaches to therapy. Retroviral vectors provide a useful vehicle for selective targeting since (1) they can only integrate into the genome of dividing cells; (2) there are no limitations in host range; and (3) these vectors have already been used successfully to infect many different cell types (for review, see Cepko, C., In *Neuromethods, Vol. 16: Molecular Neurobiological Techniques,* Boulton et al., (eds.), Clifton, N.J. , The Humana Press, pp. 177–218 (1983); Gilboa, E., *BioEssays* 5:252–257 (1987); Friedmann, T., *Science* 244:1275–1281 (1989)). The retrovirus vectors are replication-defective and can be packaged into infectious retroviral particles by transfected cell lines which contain retroviral sequences coding for the proteins necessary for the packaging of retroviral RNA, but which cannot package their own RNA (e.g., Mann et al., *Cell* 33:153–159 (1983); Danos et al., *Proc. Natl. Acad. Sci. USA* 85:6460–6464 (1988)). Since retroviruses and vectors derived from them integrate into the host cell genome, their sequences are transmitted to all daughter cells. This feature of retroviruses has been successfully used, for example, to trace cell lineages in the nervous system (Price et al., *Proc. Natl. Acad. Sci. USA* 84:156–160 (1987); Luskin at al., *Neuron* 1:635–647 (1988); Walsh et al., *Science* 241:1342–1345 (1988)).

The herpes simplex virus type 1 (HSV-1) thymidine kinase (TK) gene offers a conditional killing mechanism for dividing cells. The selective advantage of using HSV-1-TK derives from the fact that this enzyme has a higher affinity for certain nucleoside analogs, such as acyclovir, ganciclovir and FIAU, than mammalian TK (McLaren et al., In *Herpes Virus and Virus Chemotherapy,* Kono, R. (ed.), Amsterdam: Elsevier, pp. 57–61 (1985)). These drugs are converted to nucleotide-like precursors and incorporated into the DNA of replicating cells, thus disrupting the integrity of the genome, and ultimately leading to cell death. Several studies have successfully made use of its conditional toxicity in developmental studies of transgenic mice (Borrelli at al., *Proc. Natl. Acad. Sci. USA* 85:7572–7576 (1988); Heyman at al., *Proc. Natl. Acad. Sci. USA* 86:2698–2702 (1989)) as a selectable marker against non-homologous recombination events in cultured cells (Capecchi, M.R., *Trends in Genetics* 5 (3):70–76 (1989)), for killing cells harboring wild-type herpes viruses (Corey et al., *N. Engl. J. Med.* 314:686–691 (1986); Corey et al., *N. Engl. J. Med.* 314:749–756 (1986)), and in selecting for herpes virus mutants lacking TK activity (Coen at al., *Science* 234:53–59 (1986)).

In this study we used rat C6 glioma cells as a model primary brain tumor type. C6 cells rapidly form a non-encapsulated, non-metastatic tumor after injection into the adult rat CNS. Further, derivative cell lines are available, which lack endogenous TK activity (C6-BUI) or bear the lacZ gene (C6-BAG), which are useful experimentally. A retroviral vector was generated in which the HSV-1-TK gene is regulated by the strong, constitutive retrovirus LTR promoter. C&BUI cells were infected with this vector and selected for TK activity by growth in HAT medium. Parental and infected cells were tested for their dose-dependent sensitivity to ganciclovir in culture and in vivo following inoculation into the rat subrenal capsule.

Materials and Methods

Vector Construction: A 2.8 kb BamHI fragment encompassing the full coding sequence, and 2 kb of the 3'non-coding region (including the polyA addition site) of the HSV-1 TK gene (from plasmid pBRTK), was cloned into the BamHI site of a retroviral plasmid, pL(X)RNL. The resulting plasmid is called pLTKRNL. The pL(X)RNL plasmid is derived from Moloney murine leukemia retrovirus (MoMLV) and Moloney murine sarcoma retrovirus (MoMSV), and contains the following elements: a retroviral packaging sequence, psi: the neomycin-resistance (neoR) gene from transposon Tn5 placed under the transcriptional control of a Rous sarcoma virus (RSV) promoter; the colEl bacterial origin of replication; and the bacterial ampicillin resistance gene. The plasmid is basically similar to those reported in Wolff et al., *Proc. Natl. Acad. Sci. USA* 86:9011–9014 (1983); Short at al., *Devel. Neurosci.* 12:34–45 (1990); and Price et al., *Proc. Natl. Acad. Sci. USA* 84:156–160 (1987); except that it uses an RSV promoter to drive $neo^R$.

The BAG retroviral vector contains the *Escherichia coli* lacZ gene under the transcriptional control of a retroviral LTR promoter, the transposon Tn5 $neo^R$ gene under the transcriptional control of the SV40 early promoter-enhancer element, and other features as above (Price at al., *Proc. Natl. Acad. Sci. USA* 84:156–160 (1987)).

Cell Culture: An ecotropic retrovirus-packaging line, psi2, was used which was derived from a mouse fibroblast line (Mann et al., *Cell* 33:153–159 (1983)). The C6 rat glioma-derived cell lines used were: C6-BU1 (Amano et al., *Exp. Cell Res.* 85:399408 (1974)), a line selected in BUdR for loss of endogenous thymidine kinase activity, and C6BUI-BAG, a derivative of C6 BUI expressing β-galactosidase activity following infection with the BAG virus. The psi2-derived line psi2-BAG-2-14 (Short et al., *Dev. Neurosci.* 12:34–45 (1990)) was used to obtain BAG virus. All cell lines were grown in Dulbecco's modified Eagle medium (GIBCO) containing 10% fetal bovine serum (FBS brand), 100 units of penicillin and 100 μg of streptomycin per ml. Neomycin-resistant cells were selected and maintained in the same medium supplemented with 1mg/ml G418 (neomycin analog, GIBCO). Cells expressing HSV-1-TK were selected by including HAT (hypoxanthine-aminopterin-thymidine, GIBCO) in the growth medium.

Transfections. Virus Production and Infections: To produce replication-defective, HSV-1-TK-bearing retroviral vectors (v-TK), 10 μg of pLTKRNL plasmid DNA were transfected into psi2 cells by the calcium phosphate coprecipitation method using glycerol shock by standard method. Transfected psi2 colonies were selected in medium containing G418. To make virus stocks, cultures were maintained in medium with G418 until they reached 80% confluency, then they were fed medium without G418 and twenty-four hours later, the virus-containing ("conditioned") medium was removed, filtered through a 0.45 μm pore size filter and stored at −70° C.

All infections were done by replacing medium on a 100 mm tissue culture dish of recipient cells with 2 ml of medium containing 4 μg/ml polybrene (Sigma) and varying amounts of virus stock.

Virus titers of the psi2-v-TK line, were determined by infecting, 6BU1 cells, and determining the number of HAT-resistant colonies obtained per unit volume of virus stock. Two HAT-resistant clones, C6TK-vTK1 and 3, were used for further studies. For the psi2-BAG lines, virus titers were determined the same way, using NIH3T3 cells, and selecting for G418 resistance.

Histochemical Staining for β-galactosidase: To visualize β-galactosidase expression, cells were fixed in 0.5% gluteraidehyde in phoshate-buffered saline, pH 7.3, for 5 minutes at room temperature, and then stained with 5-bromo4-chloro-3-indoyl-B-D-galac to side for 30 minutes to 4 hours at 37° C. (Turner and Cepko, *Nature* 328:131–136 (1987)).

Ganciclovir Sensitivity Assays in Culture: The following cell lines; C6, CC6BU1, C6VIK1 and 3, were assayed for dose-dependent toxicity of the nucleoside analog ganciclovir (Cytovene, Burroughs Wellcome). Cells were plated at a density of 100 per 100 mm dish. Seventy-two hours later, ganciclovir was added at varying concentrations to each dish, and the incubation was continued for 9 days, changing the ganciclovir-containing medium every 3 days. The concentrations of ganciclovir tested were: 0, 3, 10, 30, 100, and 300 μm, in triplicate. On the 9th day, the medium was removed, the dishes were washed with PBS, fixed with 100% methanol for 10 minutes, stained with a 1:10 dilution of Giemsa (Fisher) in distilled water for another 10 minutes, washed again with water, then dried (Freshney, R. I., *Culture of Animal Cells—A Manual of Basic Technique,* 2nd ed., New York, Alan R. Liss, Inc. (1987)). Colonies were counted and the number on dishes with no ganciclovir was taken to represent 100% survival.

Results

Vector Construction: The integrity and orientation of the HSV-1 TK gene in the plasmid pLTKRNL were confirmed by restriction mapping. Upon cleavage with BamHI, two bands of approximately 2.8 kb and 6.7 kb were obtained, as expected from the respective sizes of the HSV-1 TK gene and the pL(X)RNL vector. Based on the sequence of the HSV-1 TK gene (McKnight, S. L., *Nucleic Acids Res.* 8(24) :5949–5964 (1980)), fragments of the expected sizes were also obtained upon cleavage with the restriction endo nucleases, PstI and SmaI. Insertion of the, HSV-1TK gene into the BamHI site of the pL(X)RN L vector placed it under the control of the MOMLV LTR promoter.

Transfection. Infection: The packaging line, psi2-TK, produced $10^4$ cfu/ml. No helper virus production by this clone could be detected. Virus from psi2-TK was used to establish C6derived (C6vTK) cell lines, which grew in HAT medium.

Ganciclovir Sensitivity in Culture: The cell lines compared in the sensitivity assay were C6, C6-BU1 and C6VIK-1 and -3.

Ganciclovir Sensitivity in vivo: Nine rats were implanted in the subrenal capsule with C6VIK cells. Four survived the procedure for further study. Tumors were measured 5 days after implantation. Two animals were treated with ganciclovir (20 mg/kg intraperitoneally daily) and two with saline daily. Tumor size was reassessed over a 16-day period. The two control tumors grew four- to twelve-fold. In contrast, the two treated with ganciclovir were smaller after the treatment than before.

Discussion

In these studies we demonstrate that a retrovirus bearing the HSV-1-TK gene can be used to confer drug sensitivity on C6 glioma cell in culture and in vivo. This is the first retrovirus vector described bearing an active HSV-1-TK gene. It should have a number of potential uses. First, as described in detail below it should prove useful in selectively delivering this "killer" gene to tumor cells in the brain. A distinct advantage of the HSV-1-TK gene as compared to other toxic gene products is that it requires a second hit, treatment with a nucleoside analogue, to effect cell death. Further, cellular DNA replication is required for toxicity, so only dividing cells can be killed. Second, it should also be possible to use this retrovirus vector to incorporate the HSV-1-TK gene into genetically modified cells used for grafting (e.g. Rosenberg et al., *Science* 242:1575–1578 (1988); This would allow elimination of the grafted cells at a defined point in the experiment to evaluate the effects of these cells on the surrounding tissue. Third, this vector should prove useful for infecting progenitor embryonic cells to assess the nature and function of their progeny at later stages in development and throughout life. This vector, then, provides a tool to efficiently infect dividing cells in culture and in vivo and to insert into their genome a gene which can be used to kill them or their progeny at a defined time by application of a drug.

Primary brain tumors affect approximately 12,000 new patients in the United States each year. Twenty-five percent of primary brain tumors are glioblastomas which are only temporarily responsive or totally resistant to all forms of currently available therapy. Glioblastomas are almost universally fatal; cures remain anecdotal with only 3-5% of patients living five years beyond diagnosis. However, metastasis from glioblastoma is exceedingly rare. Glioblastomas kill from local growth, and, in many cases treated with radiation or chemotherapy, tumors recur within 2 centimeters of the original site. This finding suggests that some tumors may be treated with a local, targeted therapeutic approach. Various attempts at local therapies have been made including local hyperthermia (Salcman et al., *J. Neuro. Oncol virol* 1:225–236 (1983))Photodynamic therapy (Cheng: et al., *Surg. Neurol.* 25:423–435 (1986)), focal irradiation with interstitial radioisotope implants (Gutin et al., *J. Neurosurg.* 67:864–873 (1987)). To date all of these techniques have met with only limited success and have had only a marginal impact on the treatment of glioblastoma.

Because of this limited success, we decided to explore retrovirus vectors as a new avenue of potential therapy. Retroviruses take advantage of the fact that a malignant glioma is a dividing cell population within the population of non-dividing cells that compose the. adult brain, thus. Retroviruses can offer a mode of selectivity for the brain tumor cells by delivering a toxic gene to them. Three toxic gene products have been used for ablation studies in transgenic mice (Bernstein and Breitman, *Mol. Biol. Med.* 6:523–530 (1989)). Two of these, ricin and diphtheria toxin, however, once released into the nervous system, could cause toxicity to brain, blood vessels, bone marrow or other tissues and cells containing them could not be aborted. For this reason, we have chosen to explore a strategy of tumor cell destruction that uses the HSV-1-TK gene, that is by itself not harmful, but which sensitizes cells to exogenously administered drugs, such as ganciclbvir. In this way cell destruction can be controlled.

We have demonstrated that the HSV-1-TK gene can be inserted into rat C6 glioma cells and that these cells are thereby made sensitive to ganciclovir. To demonstrate that C6 glioma cells expressing the HSV-1-TK gene can be killed in vivo, we used the subrenal capsule assay system in rats because it allows direct measurement of tumor volume, permits detection of small (<1mm) volume changes, and because tumor vascularization is observable and allows for entry of parenterally-administered pharmaceutical agents. This model overcomes the problems of not being able to directly observe the size of an intracerebral tumor implant and the concerns about delivery of ganciclovir through an intact blood-brain barrier. With this subrenal capsule model, we demonstrated that ganciclovir administered intraperitoneally will kill growing C6 glioma cells.

EXAMPLE 2

Glioblastomas represent approximately 30% of primary brain tumors in adults (Schoenberg, B. S., In *Oncology of the Nervous System,* Walker, M. D. (ed.), Boston, Mass. Martinus Nijhoff (1983). They are invasive, malignant, and resistant to conventional treatment modalities, and therefore are considered virtually incurable DeVita et al., *Cancer: Principles and Practice of Oncology,* Vol. 2, 3rd ed., Philadelphia: Lippincott Press (1983); Shapiro et al., *J. Neurosurg.* 71:1–9 (1989); Onoyama et al., *Am. J. Roentgenol.* 126:481–492 (1976); Salazar at al., Int. *J. Rad. Oncol. Biol. Phys.* 5:1733–1740 (1979); Walker et al., *N. Engl. J. Med.* 303:1323–1329 (1980). Recurrent disease often occurs within 2 cm of the original site (Hochberg et al., *Neurol.* 30:907–911 (1980). With a median survival of less than a year and with only 5% of patients living after five years following diagnosis despite numerous multi-modal approaches (Mahaley et al., *J. Neurosurg.* 71:826–836 (1989); Schoenberg, B. S., In *Oncology of the Nervous System,* Walker, M.D. (ed.), Boston, Mass. Martinus Nijhoff (1983); Kim et al.,*J. Neurosurg.* (in press); Daumas-Duport et al., *Cancer* 62:2152–2165 (1988)), the need for novel treatment strategies cannot be overemphasized.

One strategy is the use of viral vectors to deliver foreign genes to modulate or to destroy glioma cells. Retroviruses provide a potential means of selectively infecting tumor cells in the adult brain, because they can only integrate into the genome of dividing cells and most adult brain cells are in a quiescent, non-receptive stage of cell growth (for review of retroviruses, see Varmus, H., *Science* 240:1427–1435 (1988)). These RNA viruses have been extensively used as vectors to deliver genes to dividing cells in culture and in embryos (for review, see Cepko, C., In *Neuromethods,* Vol. 16, Molecular *Neurobiological Techniques,* Boulton, A. A., Boulton (eds.), Clifton, N.J. Humana (1989); Gilboa et al., *BioTechniques* 4:504–512 (1986)). Foreign genes and promoter elements can be inserted into plasmid DNA equivalents of the retroviral genome, which retain the packaging signal, psi. These plasmids are then transfected into packaging cell lines, which carry wild-type retroviral sequences lacking the psi element needed for packaging of their own RNA into virion particles (Cone at al., *Proc. Natl. Acad. Sci. USA* 81:6349–6353 (1984); Miller et al., *Mol. Cell. Biol.* 6:2895–2902 (1986); Mann et al., *Cell* 33:153–159 (1983)). The packaging line can insert the psi-bearing RNA encoded in the foreign gene-bearing retrovirus sequences into virion particles. These lines then release into the medium only replication-defective virions containing foreign gene sequences and no replication component virions. These replication-deficient virions can efficiently infect other dividing cells and insert the foreign genes into their genome.

A number of retroviral vectors have been developed for neuroscience applications, including ones bearing the genes for the histochemical marker, lacZ (Price et al., *Proc. Natl. Acad. Sci. USA* 84:156–160 (1987)), nerve growth factor (Wolf et al., *Mol. Biol. Med.* 5:43–59 (1988); Rosenberg et al., *Science* 242:1575–1578 (1988)), tyrosine hydroxylase (Wolff et al., *Proc. Natl. Acad. Sci. USA* 86:9011–9014 (1983); Horellou et al., *Proc. Natl. Acad. Sci. USA* 86:7233–7237 (1983); and other proteins (Fredericksen et al., Neuron 1:439–448 (1988); Cepko, C., In *Neuromethods,* Vol. 16, *Molecular Neurobiological Techniques,* Boulton, A. A., Boulton (eds.), Clifton, NJ: Humana (1983); Cepko, C., *Ann. Rev. Neurosci.* 12:47–65 (1989)). Direct injection of lacZ bearing retroviruses (e.g., BAG) into embryonic tissues in vivo can yield gene delivery into neuroblasts and their differentiated daughter cells, as observed, for example, in epithelium, retina and cerebral cortex (Gray, G. E., *Proc. Natl. Acad. Sci. USA* 85:7356–7360 (1988); Turner at al., *Nature* (Lond.) 328:131–136 (1987); Walsh at al., *Science* 241:1342–1345 (1988); Luskin et al., *Neuron* 1:635–647 (1988)). No labelling of cells has been reported following injection of this type of vector into adult nervous tissue, as anticipated from the low mitotic index of these cells and the relatively short half-life of retrovirus particles (–4 hr in culture; Cepko, C., In *Neuromethods,* Vol. 16, *Molecular Neurobiological Techniques,* Boulton, A. A.,Boulton (eds.), Clifton, N. J. Humana (1989)). Several studies have shown that it is possible to use their retrovirus vectors for indirect "gene delivery" into adult rodent brains, by infecting dividing cells in culture and then grafting these genetically modified cells into the brain (Gage at al., *Neuroscience* 23:795–807 (1987). This procedure has been used with the lacZ vector to follow the fate of grafted rat C6 glioma cells and fibroblasts (Shimohama et al., *Mol. Brain Res.* 5:271–278 (1989)). Rat fibroblast lines infected with NGF and TH-bearing vectors, rat pheochromocytoma cells infected with the NGF vector, and a mouse pituitary line infected with a TII vector, have been used to deliver biologically active NGF and/or L-dopa and dopamine to regions of adult rat bra regions of adult rat brain (Rosenberg et al., *Science* 242:1575–1578 (1988); Wolff et al., *Proc.*

Natl. Acad. Sci. USA 86:9011–9014 (1989); Horellou et al., Eur. J. Neurosci. 2:116–119 (1990)). Several new multipotent neural cell lines have been developed following infection with retrovirus vectors bearing myc and SV40 T oncogenes (Snyder et al., Neurosci. Abst. 9:9 (1989); Lendahl at al., Cell 60:585–595 (1990); Ryder et al., J. Neurobiol. 21:356–375 (1990)).

In this study we have used a rodent glioma model to explore the possible use of retroviral vectors to deliver foreign genes to tumor cells in vivo. The BAG retrovirus vector was used to deliver the reporter gene lacZ into rat glioma cells implanted into the adult rat brain. We have evaluated infection of endogenous brain cells and C6 glioma cells following direct injection of the BAG retrovirus or grafting of the psi 2-BAG packaging line which releases this virus vector. Cultured cells and tissue sections were evaluated by histochemical staining for bacterial beta-galactosidase, as an index of successful gene delivery, and by immunostaining for glial fibrillary acidic protein (GFAP) and S100, as a marker for glioma cells and astrocytes (Bignami et al., Brain Res. 43:429–435 (1972)), and for fibronectin, as a marker for the fibroblast-derived packaging line.

Materials and Methods

Cell culture. retrovirus infection and beta-galactosidase staining. The ecotropic retrovirus producer line, Psi 2-BAG 2-14, obtained through M. Rosenberg (UCSD) from C. Cepko (Harvard Medical School) (Price et al., Proc. Natl. Acad. Sci. USA 84:156–160 (1987); Short et al., Dev. Neurosci. 12:3445 (1990)), was grown in Dulbecco's modified Eagle's medium, 10% fetal calf serum, with 100 units penicillin, 100 $\mu$g/ml streptomycin (D10 P/S), and 500 $\mu$g/ml of the neomycin analogue, G418. All cell culture materials were obtained from GIBCO. Virus was harvested by replacing the overlying media of nearly confluent cultures with a reduced volume of fresh media without G418. The conditioned media containing viral particles was removed 24–48 hr later, filtered through cellulose acetate membranes (pore size 0.45 $\mu$m, Nalgene) and stored at −70° C. The virus was titered as colony-forming units (cfu) on 3T3 cells in the presence of G418. Viral titers were 1–3×10$^4$ cfu/ml. In some cases, viral stock was concentrated by centrifugation (Price et al., Proc. Natl. Acad. Sci. USA 84:156–160 (1987)) to 1–3×10$^5$cfu/ml.

Rat glioma cell line, C6 (Benda et al., Science 161:370–371 (1968)), was grown in D10 P/S. A C6-BAG line was prepared by infecting C6 glioma cells with the BAG vector, and isolating single cell subclones under G418 selection. Cells were assayed for beta-galactosidase activity by histochemical analysis (Price et al., Proc. Natl. Acad. Sci. USA 84:156–160 (1987)). A subclone (C6-BAG B2-10) in which >99% of cells were beta-galactosidase positive after at least 6 passages was used in subsequent experiments at passage 2 or 3.

Cell grafting and retrovirus inoculation into adult rat brain. Adult Fischer rats weighing between 151–175 gms were anesthetized with an intraperitoneal injection of Equithesin (Short, C., Principles and Practice of Veterinary Medicine, Williams and Wilkins, Baltimore, Md. (1987)). Two to five animals were used for each experimental paradigm, and all experiments were carried out at least twice. Stereotactic coordinates for intracerebral injection were taken from a stereotactic atlas of the adult rat (Paxinos et al., In Rat Brain in Stereotaxic Coordinates, 2nd ed., Academic Press, New York (1986)). Cells and virus were injected with 8 $\mu$g/ml polybrene, or control medium using a 10 $\mu$l Hamilton syringe with a beveled 25 gauge needle. Injections (5$\mu$l) were done over a 5 min interval, and the needle was kept in place for another 2 min prior to removal. Surgery was tolerated well by most animals; only a few animals died during anesthesia.

For grafting experiments, confluent cultures were rinsed with Dulbecco's phosphate-buffered saline (PBS) without Ca++ and Mg++ and incubated with 0.05% trypsin. Cells were dispensed in D10 and pelleted by centrifugation for 5 min at 1200×g. Cell pellets were resuspended in PBS and collected by centrifugation. Final cell suspensions were made at a density of 10$^5$ cells/$\mu$l in complete PBS (PBS, which contains 1 $\mu$g/ml each MgCl$_2$ and CaCl$_2$, 0.1% glucose, and 5% rat serum (GIBCO)) and maintained at 4° C. until implantation.

Tissue preparation. Prior to perfusion, rats were anesthetized with Equithesin (Short, C., Principles and Practice of Veterinary Medicine, Williams and Wilkins, Baltimore, Md. (1987)). Perfusion was done via the ascending aorta with 50 ml of cold PBS containing 10,000 units/ml sodium heparin followed by 250 mi of cold 3% paraformaldehyde in PBS. After post fixation overnight at 4° C., brains were kept in increasing percentages (15, 20, 30) of sucrose at 4° C. until they sank. Brains were frozen on dry ice and kept at −80° C. until sectioning. Sections was either cut at 40 $\mu$m on a freezing microtome and kept at 4° C. in 0.5 M. Tris-HCI, pH 7.4, with 0.1% sodium azide or in 33% polyethylene glycol until staining; or cut at 10–15 $\mu$m on a cryostat and mounted directly onto gelatin-subbed (Fisher; 100 Bloom) slides and stored at 4° C. with desiccant until staining.

Histology. For beta-galactosidase histochemistry of tissues (and cells), a modification of the method of Turner and Cepko (Turner et al., Nature (London) 328:131–136 (1987)) was used. Briefly, 5-bromo-4-chloro-3-indoly B-D-galactoside (X-gal,:Boehringer Mannheim) was prepared as a 4% stock solution in DMSO. Free-floating or mounted sections (or cells on tissue culture dishes) were incubated at 37° C. in a solution of PBS containing 2$\mu$M MgCl$_2$, 35 $\mu$M K$_3$Fe(CN)$_6$, 35 $\mu$M K$_4$ Fe(CN)$_6$, 0.01% sodium deoxycholate, and 0.02% NP4O, pH 7.3; 0.1% X-gal was added just prior to incubation. After incubation overnight at 37° C., cultured cells were viewed directly and sections were rinsed with PBS, mounted on subbed slides and then counterstained with hematoxylin and eosin or neutral red. They were then rinsed in water, cleared in increasing concentrations of alcohol, and placed in water prior to coverslipping with aqueous mounting media, Crystal Mount (Biomedia) or placed in xylene prior to coverslipping with Permount (Fisher).

Some sections were also stained immunocytochemically to identify GFAP, S100 or fibronectin. The sections were rinsed in PBS, incubated for 30 min with blocking serum and then overnight at room temperature with the following antibodies: mouse monoclonal antibodies to human GFAP (Boehringer Mannheim), diluted 1:3; rabbit polyclonal antibody to bovine S100 (Dako) diluted 1:750, or mouse monoclonal antibody to human fibronectin (Cappell) diluted 1:80; all of which crossreact with their respective rat antigens. Antibodies were diluted in 10$\mu$M phosphate buffer, pH 7.4, containing 0.9% NaCl, 0.25% Triton-X and 3% blocking serum. After thorough rinsing the sections were incubated for 2 hr with either biotinylated horse antimouse IgG, biotinylated goat antirabbit IgG, or rabbit antigoat IgG (Vectastain) diluted 1:200 in the buffer, followed by several rinses in PBS. The sections were then incubated for 30 min with a complex of avidin and biotinylated horseradish peroxidase (Vectastain, ABC elite kit) diluted 1.5:100 in the buffer. The peroxidase was visualized by reacting with 0.05% 3,3-diaminobenzidine tetrahydrochloride, 0.04% $NiCl_2$ and 0.01% $H_2O_2$ in 50 μM Tris-HCI, pH 7.3, for 5–10 min at room temperature. In some cases, sections were initially stained histochemically for beta-galactosidase activity and then immunostained for GFAP. In other cases, serial selections were stained alternatively for beta-galactosidase and GFAP or S100.

Results

Histochemical staining of psi 2BAG cells in culture demonstrated nearly 100% positive staining for beta-galactosidase and no staining for GFAP, while most C6 cells stained positively for GFAP antigen, and all were negative for beta-galactosidase staining under the neutral conditions used. The ability of the psi 2-BAG cells to release BAG virus that could infect C6 cells was demonstrated by placing coverslips containing each of these two cell types at separate locations within the same culture dish. In the presence of psi 2-BAG cells, an ever-increasing percentage of cells on the coverslip bearing C6 cells stained positively for beta-galactosidase over a 96-hr period. Essentially, all cells on the glioma coverslip were also GFAP-positive. This is consistent with successful integration of the BAG virus released by psi 2-BAG cells into glioma cell genomes.

The efficiency of gene transfer to endogenous brain cells in vivo was tested by direct inoculation of 5 μl BAG retrovirus vector (90–900 cfu) into adult rat hippocampus or caudate. Control animals were similarly inoculated with complete PBS. Animals were sacrificed 7 days after injections. In the animals which received direct injection of virus, as well as in control animals, no cells positive for beta-galactosidase were seen within the parenchyma. Some sections from both groups revealed faint positive staining for beta-galactosidase within the choroid plexus, as noted previously (Shimohama et al., *Mol. Brain Res.* 5:271–278 (1989)). In these control sections the stain was qualitatively different than in animals in which positively staining cells are present within the tumor mass (see below).

The efficiency of direct inoculation of tumor cells in the brain was tested at varying intervals between the time of the C6 cell implants and injection of the virus, under the assumption that the glioma cells might experience a growth lag after inoculation and thus not initially be in a stage of cell division appropriate for viral integration. The site of implantation and infection was the right frontal lobe. For simultaneous injections of glisoma cells and BAG virus, C6 cells ($5 \times 10^5$) were suspended in 5 μl of viral stock (90–900 cfu). Other animals received delayed injections of virus stock into the previous site of the C6 cell implant. Five μl aliquots of virus stock were injected using the same stereotactic coordinates with which the C6 cells had been implanted 3 and 5 days previously. Control animals received grafts of C6 or C6-BAG cells without virus. All animals were sacrificed seven to 10 days after the last viral injection. In simultaneous injections of C6 cells and BAG virus, only a few tumor cells (less than 0.1%) stained for betagalactosidase activity. In some cases, stained endothelial cells were also noted in vessels within and around the tumor mass. In the animals in which there was a delay between the tumor implant and the virus injection, again only a few positive cells were seen. There was no notable difference between the numbers of positively staining cells in animals which had experienced a delay before the viral injection versus those which received co-injections of C6 and BAG virus. Injections of C6 and C6BAG cells gave rise to tumors of similar size. In the C6 cell injections without virus, no blue cells were seen; in the C6BAG injections, all tumor cells were positive for beta-galactosidase, as noted previously (Shimohama et al., *Mol. Brain Res.* 5:271–278 (1989)).

To examine the fate of grafts of psi 2-BAG packaging cells, animals were injected with psi 2-BAG cells ($5 \times 10^5$ cells) into the right front lobe, and as a control, with an equal number of psi 2 cells into the left frontal lobe. Animals were sacrificed at varying times after implantation. After one day, a compact mass of beta-galactosidase positive cells were seen at the site of the right frontal injection. No positively stained cells were seen on the left side on day one, nor in either side in sections taken from animals sacrificed at days 5, 9, 14, and 21 following implantation. There was no evidence of tumor formation or other degenerative changes on the brain over this period.

The efficiency of in situ gene transfer of the lacZ gene into C6 by co-grafting of packaging line, psi 2-BAG, was then tested. For simultaneous co-grafts, the cell suspension contained a mixture of cells, in a ratio of one C6 cell to five psi 2-BAG cells. The site of implantation was again the right frontal lobe. For delayed injections, animals received implants of C6 cells ($2 \times 10^5$ cells) on day one, followed by injections of 5 μl of psi 2-BAG cells ($5 \times 10^5$ cells) on days 3 or 7. In all cases, animals were sacrificed seven days after psi 2-BAG cells had been implanted. Controls of psi 2-BAG and C6 alone were injected into other animals in parallel. In histochemically stained sections from animals which received simultaneous co-grafts of C6 and psi 2-BAG cells, both blue and non-blue cells were seen within the tumor mass. Some of these beta-galactosidase positive cells co-stained for GFAP or S100, indicating they were C6 glioma cells. There were also many GFAP or S100 positive cells within the tumor mass which were not positive for beta-galactosidase. Some of the other beta-galactosidase positive cells could be C6 cells with no or low expression of GFAP, or S100. In fact, in C6 cells implanted alone into the brain, only about half of the cells in the resulting tumor mass were S100-positive and even fewer were GFAP positive. Some of the beta-galactosidase positive cells could also be psi 2-BAG cells which might have survived longer within the tumor mass as compared to the brain parenchyma; however, immunostaining for fibronectin revealed no psi 2-BAG cells in co-grafts after 7 days. Examination of serial sections of these tumors revealed many sections without any beta-galactosidase-positive cells, and our best estimate is that about 1% of the cells in the tumor expressed the lacZ gene in animals receiving simultaneous injection of psi 2-BAG cells and C6 cells. In contrast, sections taken from animals which had received delayed injections of the packaging line into the tumor mass contained many cells positively stained for beta-galactosidase in all sections throughout the tumor, with up to 10% of cells being positive and most positive cells at the periphery of the tumor. Co-staining for the glia-specific antigen S100 and betagalactosidase revealed that many of the cells within the tumor were glia-derived and some of these were also positive for beta-galactosidase activity. Tumor cells thus appear to have been more efficiently infected when the packaging line was grafted after establishment of tumor cells than when tumor and packaging cells were simultaneously injected. There did not appear to be any significant difference between animals in which the delay between injections was three days as opposed to seven days.

Discussion

In this study we have demonstrated the efficacy of a replication-defective retroviral vector in delivering the reporter gene, lacZ, to rat glioma cells in culture and the rat brain. In culture, the BAG retrovirus vector released from psi 2-BAG cells successfully infected C6 cells in the same dish, as demonstrated by staining for beta-galactosidase activity. The morphology and immunoreactivity to GFAP confirmed the identity of the beta-galactosidase positive cells as glioma cells. The efficiency of transfer of the lacZ gene to endogenous brain cells or to C6 cells in vivo was then compared by two techniques: direct injection of BAG virus or grafting of the packaging line which releases the virus. The highest efficiency in vivo was obtained by grafting of the retrovirus packaging line into an established bed of C6 tumor cells.

Initial attempts to deliver the reporter gene by direct injection of virus into the parenchyma of a normal adult rat brain produced essentially no beta-galactosidase-positive cells. In these animals, as well as in controls inoculated with complete PBS, faint positive staining was seen in the choroid plexus, but not in the parenchyma. This endogenous positive staining of lysosomal betagalactosidase has been previously reported (Shimohama et al., *Mol. Brain Res.* 5:271–278 (1989)), and was masked when sections were counterstained with neutral red. The unsuccessful direct gene delivery by the viral vector was not surprising since the majority of cells in adult rats, even in young postnatal animals, are post-mitotic, and cell division is needed for retroviral integration. The site of inoculation, the hippocampus, was chosen to enhance the likelihood of successful integration, since cells in this region are the last to stop dividing after birth (Das et al., *Brain Research* 22:122–127 (1970)). In animals inoculated with the BAG virus either simultaneously with glioma cells or after a delay following the glioma implant, only a few isolated tumor cells were successfully infected. This presumably reflects the relatively short half-life of the retrovirus in vivo and the state of division of the glioma cells. Of the few beta-galactosidase positive cells, most were found at the edges of the tumor where there is thought to be highest mitotic activity. Occasionally stained endothelial cells were observed, which would be expected since endothelial cells continue to divide within the blood vessels of the brain, especially in a vascularized tumor bed.

Both viral titer and the volume of the inoculum represent significant limitations to attaining a higher degree of successful integration using direct virus injection. Attempts to increase viral titer by centrifugation only increased the titer by 10- to 100-fold. When inoculating a glial tumor, which began with about 105 cells, with 5 $\mu$l of a retrovirus stock of $10^4$–$10^6$ cfu/ml, the ratio of virus to cell is much less than one to one (multiplicity of infection MOI)$\leq$0.01). In our hands, the efficiency of infection of rapidly dividing C6 cells in culture with the BAG retroviral vector at an MOI of 3 is approximately 30%. Thus it is not surprising that direct inoculation of the tumor was inefficient in vivo.

Implantation of the packaging line appears to overcome some of the limitations of direct inoculation by releasing the virus within the tumor over a prolonged period. This study demonstrates that co-grafting of the packaging line, psi 2-BAG and glioma cells, serves to deliver the reporter gene, lacZ, to these tumor cells more efficiently than direct viral inoculation. The efficiency was greater in animals implanted with glioma cells 3 or 7 days prior to implantation of psi 2-BAG cells as compared to simultaneous grafting of these two cell types. Histochemical analyses of sections taken from the brains of animals, which had received delayed injections, showed that large areas of the tumor were successfully infected. The brains were examined one week after the psi 2-BAG implantation, because in a separate experiment when psi 2-BAG cells were implanted alone, they were undetectable five days later. Further, immunostaining of co-grafts after 7 days revealed no fibronectin positive cells. This suggests either that the psi 2-BAG graft had been immune rejected because of a difference in rat strains or that the retroviral encoded gene, if present, was no longer being expressed (Palmer et al., personal communication). By immunocytochemistry, we have established that some of the cells within the tumor stain for both beta-galactosidase activity and GFAP or S100 antigens, confirming successful infection of glioma cells by the BAG virus released from the psi 2-BAG cells. However, there are GFAP- and S100-positive cells within the tumor which are beta-galactosidase negative, suggesting incomplete infection of tumor cells.

Several means can be envisioned to increase the efficiency of infection of glioma cells in the brain by co-grafting of retrovirus packaging lines. One way would be to carry out a series of injections of the packaging line to increase the number of cells releasing virus within the tumor bed over a longer period. Another way to increase the amount and duration of retrovirus release would be to develop a packaging line which was immune compatible with the host and thus would survive longer following grafting. Release to a larger area including the brain parenchyma surrounding the tumor might also be achieved by using an astrocyte-derived packaging line. Grafted newborn and embryonic astrocytes have been shown to be able to migrate up to 5 mm from their original site of injection and may be better than fibroblasts in reaching infiltrating glial tumor cells (Jacque et al., *Dev. Neurosci.* 8:142–149 (1986); Zhou et al., *J. Comp. Neurol.* 292:320–330 (1990); Hatton et al., *Soc. for Neurosci. Abstracts* 15: 1369 (1989)). Additionally, a glial-derived packaging line derived from glia which are endogenous brain cells, may have enhanced survival, and may be more responsive to in situ cues. In the case of spontaneous brain tumors, one could envision a scheme in which the tumor mass was removed, leaving some tumor cells behind, and the packaging line grafted directly into the lesion. This would serve to increase the number of packaging cells that could be grafted in and the ratio of packaging cells to tumor cells, and hence increase the ability to infect tumor cells.

This study represents a model system that could be used to deliver genes with therapeutic potential to malignant glial tumors of the central nervous system (CNS), which at this time continue to pose a unique challenge in oncology. Complete surgical extirpation is impossible, since the tumor cells infiltrate within the normal brain. Radiation therapy is limited by the sensitivity of the normal brain to radiation damage. Chemotherapy is hampered by the presence of a blood brain barrier decreasing the usefulness of agents unable to cross this barrier to reach infiltrating tumor cells. Retroviruses represent potential therapeutic agents which can confer genetic susceptibility onto tumor cells. One example would be a retrovirus packaging line that releases virions containing the herpes simplex virus thymidine kinase (HSV-TK) gene (Moolten et al., *J. Natl. Cancer Inst.* 82:297–300 (1990)). When integrated into the mammalian cell genome, the HSV-TK gene confers sensitivity to chemotherapeutic agents, such as the nucleoside analogues, acyclovir, ganciclovir, and FIAU (Borrelli et al., *Nature* 339:538–541 (1989); Moolten, F., *Cancer Res.* 46:5276–5281 (1986)). Cell culture studies have shown that C6 glioma cells and other cells infected with this retrovirus are killed at concentrations of ganciclovir 100-fold less than those required to kill uninfected cells (Moolten et al.,*J. Natl. Cancer Inst.* 82:297–300 (1990)).

It may also be possible to kill C6 glioma cells by subsequent cografting of the HSV-TK virus packaging line and treatment of animals with a nucleoside analogue. Further, tumor vessels may be an additional target for a proposed killing system using the HSV-TK gene.

EXAMPLE 3

Retroviral vectors can be used to transfer genes into the genome of dividing cells. In order to increase the efficiency of gene delivery and killing effect of ganciclovir, we developed a new packaging line (C6VIK-WT) by infecting C6VIK cells with an ecotropic wild-type retrovirus (MoMLV). See, Mann et al., Cell 33:153–159 (1983); Price et al., Proc. Natl. Acad. Sci. USA 84:156–160 (1987); and Cepko, C., In Neuromethods: Molecular Neurobiological Techniques, Vol. 16, Boulton et al., eds. (Clifton, N.J., Humana), pp. 177–219. Because tumor cells can migrate deep into brain parenchyme, they should be able to deliver the vector to tumor cells away from the tumor mass. In culture, 50% of C6VIK-WT cells were killed at 0.024 $\mu$M GCV, while it took 7.3 $\mu$M GCV to kill 50% of C6VIK cells. This suggests that C6VIK-WT cells may have more HSV-TK activity than C6VIK due to multiple integrations of the HSV-TK gene or to an increased sensitivity of C6VIK-WT cells to GCV toxic products. When C6VIK and C6VIK-WT were cultured with C6BAG cells (labelled with the lacZ gene and thus detectable by beta-galactosidase histochemistry), following GCV treatment substantially more C6BAG cells were killed when co-cultured with C6VIK-WT than with C6VIK cells. Presumably C6VIK-WT cells produce both wild-type retrovirus and retrovirus vectors containing the HSV-TK gene (neither of which are produced by C6VIK cells) and death of C6BAG cells might be mediated by retrovirus infection and/or self-generated GCV toxic products. In vivo GCV treatment caused regression of tumors in most nude mice inoculated subcutaneously with C6VIK-WT cells, or with C6VIK-WT and C6BAG cells simultaneously but not with C6BAG cells alone. These findings suggest the efficiency of retrovirus-mediated gene delivery and the sensitivity to toxic agents of tumor cells can be increased using helper virus, which turns cells infected with retrovirus vectors into packaging cell lines.

The use of retroviral vectors for gene delivery need not be restricted to gene systems designed for tumor destruction. Delivery of genes involved in tumorigenesis or tumor modulation may also be a useful strategy to explore. The loss of heterozygosity for DNA markers on chromosomes 17, 10 and, less commonly, chromosome 22, in glial tumors suggests that tumor suppressor genes reside in these chromosomal regions (Bigner et al., Hereditas 101: 103–113 (1984); Bigner et al., Cancer Res. 88:405–411 (1988); James et al., Cancer Res. 48:5546–5551 (1988); El-Azouzi et al., Proc. Natl. Acad. Sci. USA 86:7186–7190 (1989)). Restoration of retinoblastoma gene function has been shown to inhibit growth of retinoblastoma and osteosarcoma cells in culture (Huang et al., Science 242:1563–1566 (1988)).

EXAMPLE 4

Presently, in order to transfer chemosensitivity to recipient tumor cells at levels which are therapeutically useful, a C6VIK glioma line infected with wild type Moloney murine leukemia virus (WT MoMLV) was used as the vector-producing or "donor" cell line. Glioma cells, being neoplastic, persist longer in vivo and intermingle with other tumor cells. Further, wild type helper virus mediates a more widespread infection of "recipient" tumor cells with the VIK vector than could be achieved with a defective helper. The infected cell line (C6BVIKWT) releases both replication-defective VIK vector and wild type virus. Presently, C6BVIKWT cells sensitize recipient C6BAG tumor. cells to ganciclovir treatment, both in culture and in vivo.

Methods

Retrovirus

The VIK retrovirus vector contains a 2.8 kb BamHI fragment containing the full coding sequence and 2 kb of the 3' noncoding region (including the poly A addition site) of the HSV-TK gene cloned into the BamHI site of the retrovirus plasmid, pLRNL, (Ezzedine et al., New Biol. 3:608–614, 1991). The BAG retrovirus vector bears lacZ transcribed from the 5' LTR and the neoR gene transcribed from an SV40 promoter-enhancer element (Price et al., Proc. Natl. Acad. Sci. USA 84:156–160, 1987). The producer cell line "sup", which releases infectious wild type MoMLV, was used (Reik et al., Proc. Natl. Acad. Sci. USA 82:1141–1145, 1985).

Cell Culture and Infection

The rat C6 glioma line was derived from a nitrosomethylurea-induced brain tumor (Benda et al., Science 161:370–371, 1969). The C6 BAG cell line was generated by infecting C6 glioma cells (Benda et al., 1969) with the BAG retrovirus and cloning under selection in G418 (see below); the cells in this clone uniformly express E. coli beta-galactosidase (Shimohama et al., Mol. Brain. Res. 5: 271–278, 1989).

The C6BU1 cell line was derived from rat C6 glioma cells by mutagenesis and selection in bromodeoxyuridine for loss of endogenous TK activity (Amano et al., Exp. Cell. Res 85:399–408, 1974). C6BU1 cells were infected with either the retrovirus vector, VIK (Ezzedine et al., New Biol. 3:608–614, 1991), or the retrovirus vector, BAG (Price et al., Proc. Natl. Acad. Sci. USA 84:156–160, 1987), produced by psi-2 producer lines, and were cloned under selection in the presence of HAT (10 mM sodium hypoxanthine, 40 $\mu$M aminopterin and 116 mM thymidine, GIBCO) or the neomycin analogue, G418 (1 mg/ml, GIBCO), respectively, to yield lines C6BVIK and C6BBAG. C6BU1 and C6VIK cells were infected with wild type MoMLV virus (WT) released from the producer line, "sup", to produce C6BWT and C6VIKWT cells, respectively. Other cell lines used in the study were NIH3T3 and TK-negative NIH3T3.

All cell lines were grown in Dulbecco's modified Eagle medium(320–1965, GIBCO) containing 10% fetal bovine serum (GIBCO), 100 units/ml penicillin, and 100 $\mu$g/ml streptomycin. All infections were done in the presence of polybrene (Sigma), as described (Mann, R., et al., Cell 33:153–159 (1983).

Viral stock was obtained from cultures grown to near 80% confluency in selection medium, then maintained in media lacking G418 or HAT for 24 hrs. Culture medium was removed, filtered through a 0.45 $\mu$m filter (Nalgene) and stored at $-70°$ C. (viral stock).

Viral titers of the producer cell lines were measured by infecting NIH3T3 (TK−) or NIH3T3 cells with virus stock and determining the number of HAT-resistant or G418-resistant cells, respectively, per unit volume of stock. Culture medium from C6V1K cells, at the same passage as used here, was shown to be absent of helper virus activity (Ezzedine et al., New Biol.3:608–614 (1991)).

Ganciclovir Sensitivity Assays in Culture

To measure the sensitivity of isolated cells, cells were plated in 24-well plates at a density of $10^4$ cells per well. The next day, medium was replaced with medium containing ganciclovir (Cytovene, Burroughs Wellcome) at varying concentrations (0–1 µM) in quadruplicate. Four days later, cells were harvested using trypsin and counted using a cell counter (Coulter Electronics Ltd., Luton, United Kingdom). Cell growth is expressed as the percentage of cells compared to the number of cells without treatment (100%).

To measure the ganciclovir sensitivity of colony formation, cells were plated in duplicate at a density of 500 cells per 25 cm$^2$ culture flask. Seven days later, ganciclovir was added at various concentrations (0, 0.1, 0.5, 1, 10, 50, 100, 300 µM) in quadruplicate and incubation was for 9–12 days, with medium changes every 3–5 days. Cells were then fixed with 100% methanol, and stained with Giemsa (Freshney, R. I., "Culture of Animal Cells," in: *A Manual of Basic Techniques,* 2d ed., New York, Alan R. Liss, Inc., pp. 170–171 (1987)), and colonies $\geq$2 mm in diameter were counted.

Co-culture Experiments

For delayed co-culture experiments, C6BAG or C6BBAG cells (recipients) were plated at a cell density of 10$^3$ cells per 25 cm$^2$ culture flask in duplicate and cultured for seven days, at which time sampling showed their numbers had increased to 5×10$^4$ cells per flask. Donor C6VIK or C6VIKWT cells were then added to the cultures at a ratio of 1:2 (5×10$^4$ recipient cells:10$^5$ donor cells). Control cultures consisted of C6BAG or C6BBAG cells alone, or C6BAG or C6BBAG cells co-plated with "donor" C6BU1 or C6BWT cells, after delay, as above. After 10 days ganciclovir was added at varying concentrations (0–300 µM) and cells were incubated for another 9–12 days with the drug. Cells were then fixed with 0.5% glutaraldehyde and stained histochemically for beta-galactosidase activity, as described (Price et al., *Proc. Natl. Acad. Sci. USA* 84:1141–1145 (1987)), and colonies were counted.

For simultaneous co-culture experiments, 103 recipient cells, C6BAG or C6BBAG were plated together with 10$^5$ C6VIK or C6VIKWT donor cells, in duplicate. Controls were C6BAG or C6BBAG cells co-plated with C6BU1 cells at a similar ratio (1:100). After seven days ganciclovir was added at varying concentrations (0 to 300 µM) and culture was processed as above. To assess the effects of the ratio of the donor cells to recipient cells, simultaneous co-culture experiments were also done varying the ratio of the donor cell, C6VIKWT, to the recipient cell, C6BAG, from 0.1 to 100.

Toxicity Assay

To assay for the generation of a diffusible cytotoxin from donor cells infected with wild type virus and/or toxic metabolites from cells bearing the HSV-TK gene treated with ganciclovir, medium was harvested from co-cultures of C6BAG and C6VIKWT cells before and during treatment with 300 µM ganciclovir for seven days. Control medium was harvested from C6BAG cells. The media were filtered (as above) and assayed for cytotoxicity to naive C6BU1 cells plated at 10$^4$ cells per 25 cm$^2$ culture flask in duplicate. Volumes of media ranged from 0.1 to 1 ml in a total volume of 4 ml/flask. After seven days, the cells were fixed with 100% methanol and Giemsa-stained, and colonies were counted.

Ganciclovir Sensitivity of Tumors In Vivo

C6VIKWT cells (5×10$^5$ cells in 200 µl media) were injected subcutaneously into the flanks of female nude mice (NCr/Sed, nu/nu; MGH breeding colony) (Ezzedine, Z. D., et al., *New Biol.* 3:608–614 (1991)). There were three treatment groups; 25 mg/kg ganciclovir intraperitoneally twice a day for 14 days, n=5; 25 mg/kg ganciclovir intraperitoneally once a day for 14 days, n=4; and 12.5 mg/kg ganciclovir intraperitoneally twice a day for 14 days, n=4. Ganciclovir therapy was begun when tumor size reached 1 cm in diameter as measured by calipers, by intraperitoneal injections up to 25 mg/kg daily for 14 days. The control group received phosphate buffered saline (PBS, 310–4200AJ, GIBCO) intraperitoneally in similar dosing schedules for 14 days. Tumor volumes were measured biweekly during treatment over a 24 day period, and were expressed as a percentage compared to the volume at the time treatment was begun.

Sequential injections of 10$^5$ C6BAG cells followed immediately by 106 C6BU1 cells, C6VIK cells, or C6VIKWT cells at the same injection site, were carried out as above using 20 animals for each combination. After the tumors had reached 1 cm in diameter, ganciclovir treatment was begun for 14 days, 25 mg/kg twice a day intraperitoneally in half of each group, with the other half receiving PBS intraperitoneally as a control. Tumor volume was assessed as the percentage increase over the volume at the beginning of treatment through 17 days.

Results

Culture Studies

Ganciclovir Sensitivity

Figure 3:
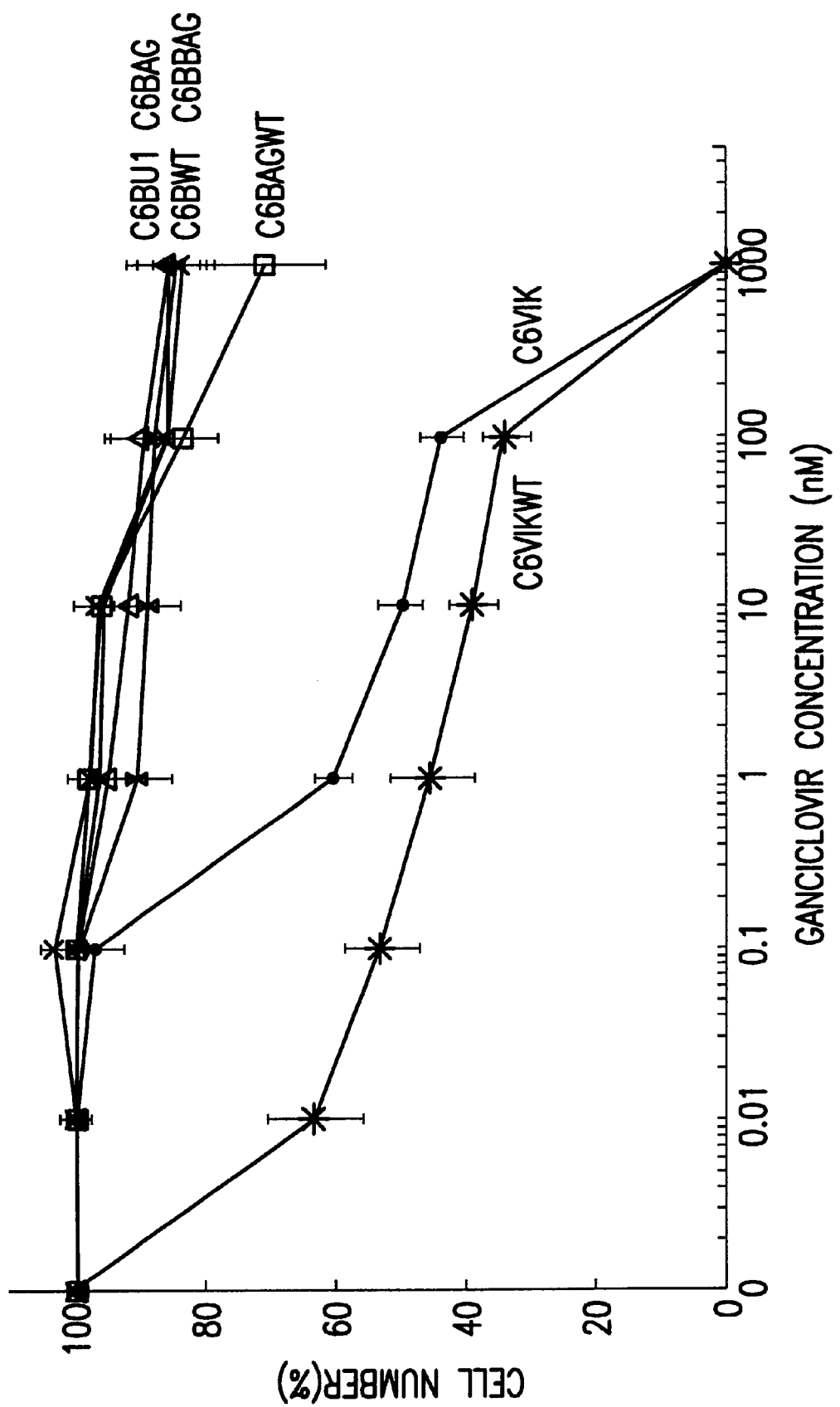
FIG. 3: Ganciclovir sensitivity of C6-derived cells in culture. Growth inhibition of C6VIK, C6VIKWT, C6BU1, C6BAG, C6BBAG, C6BAGWT and C6BWT cells by ganciclovir when treatment was begun the day after plating. Cell numbers were determined four days after plating. Cell growth is expressed as the percentage of cells with treatment compared to the number of cells without treatment (100%). Bars indicate standard error of the mean.
Figure 4:
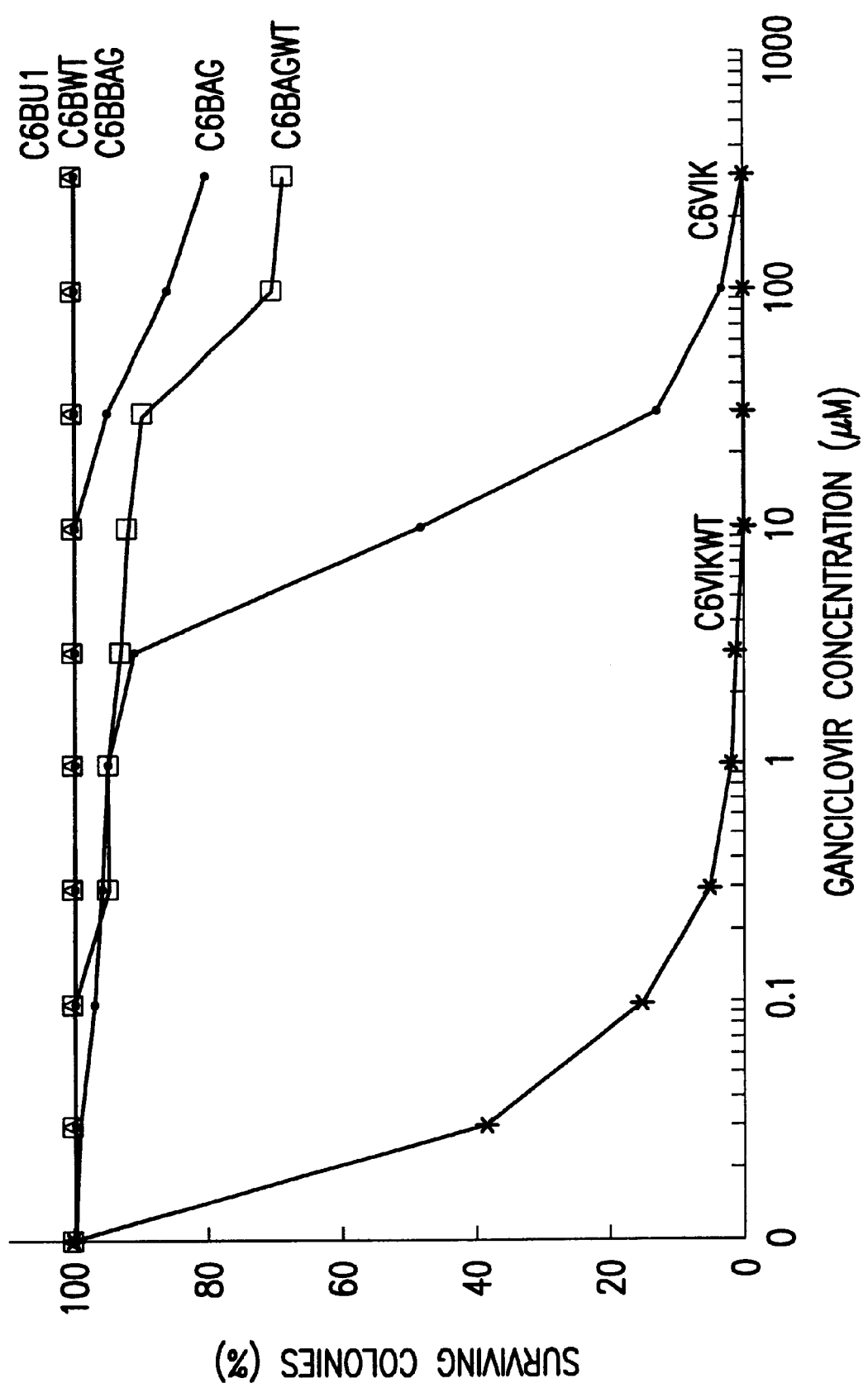
FIG. 4: Ganciclovir sensitivity of C6-derived cells in culture. Ganciclovir treatment was begun 7 days after plating these same cell lines to determine the ganciclovir sensitivity of colony formation. Ganciclovir treatment was continued for 9–12 days and then colonies were stained and counted. Survival colonies are expressed as a percentage compared to the number of colonies without treatment (100%). Studies were done in triplicate with less than 0.5% variability.

The dose dependent sensitivity of various cells lines to ganciclovir was evaluated by cell proliferation and colony formation assays. Of the two HSV-TK bearing lines, C6VIKWT cells were more sensitive to ganciclovir than C6VIK cells in the proliferation assay (FIG. 3). Fifty percent inhibition of growth over a four-day period was seen for C6VIK cells at 10 nM, and for C6VIKWT cells was 0.3 nM. No substantial inhibition of growth was found for the C6BU1 (HSV-TK negative), C6BAG, C6BWT, C6BBAG or C6BAGWT cells even at 1000 nM ganciclovir. For colony survival, drug therapy was begun seven days after plating, then nine to 12 days later surviving colonies were counted. The cell line C6VIKWT, was 300-fold more sensitive to the toxic effect of ganciclovir than the parental line C6VIK, when evaluated at the level of 50% surviving colonies (FIG. 4). The much greater sensitivity of C6VIKWT as compared to C6VIK cells is related to the presence of the HSV-TK gene since there was no significant difference in sensitivity of C6BAGWT and C6BWT lines, which had been similarly infected with the wild type virus, when compared with uninfected C6BAG and C6BU1 cells (FIG. 4).

Figure 5:
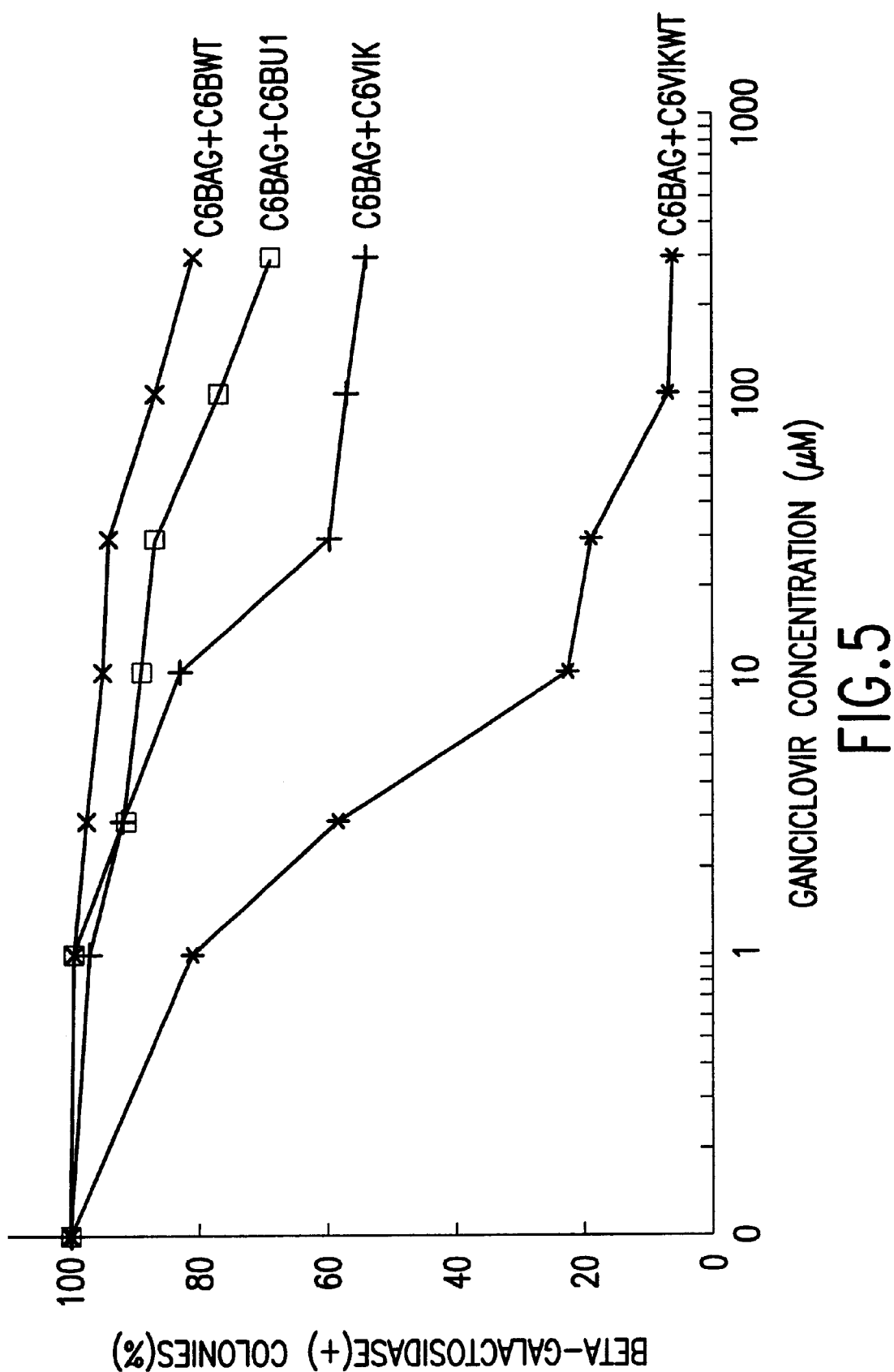
FIG. 5: Ganciclovir sensitivity of C6BAG cells after delayed co-culturing with other C6-derived lines. Seven days after C6BAG cells recipients were plated, C6BU1, C6BWT, C6VIK, or C6VIKWT cells (donors) were plated with them at a ratio of 1:2. Ganciclovir treatment was begun three days later and continued for 9–12 days. Cells were then stained for beta-galactosidase activity and only positive colonies were counted. Colony numbers are expressed as a percentage of those seen for parallel cultures without ganciclovir. Only survival of beta-galactosidase-positive colonies was scored. Studies were done in triplicate with less than 0.5% variability.
Figure 6:
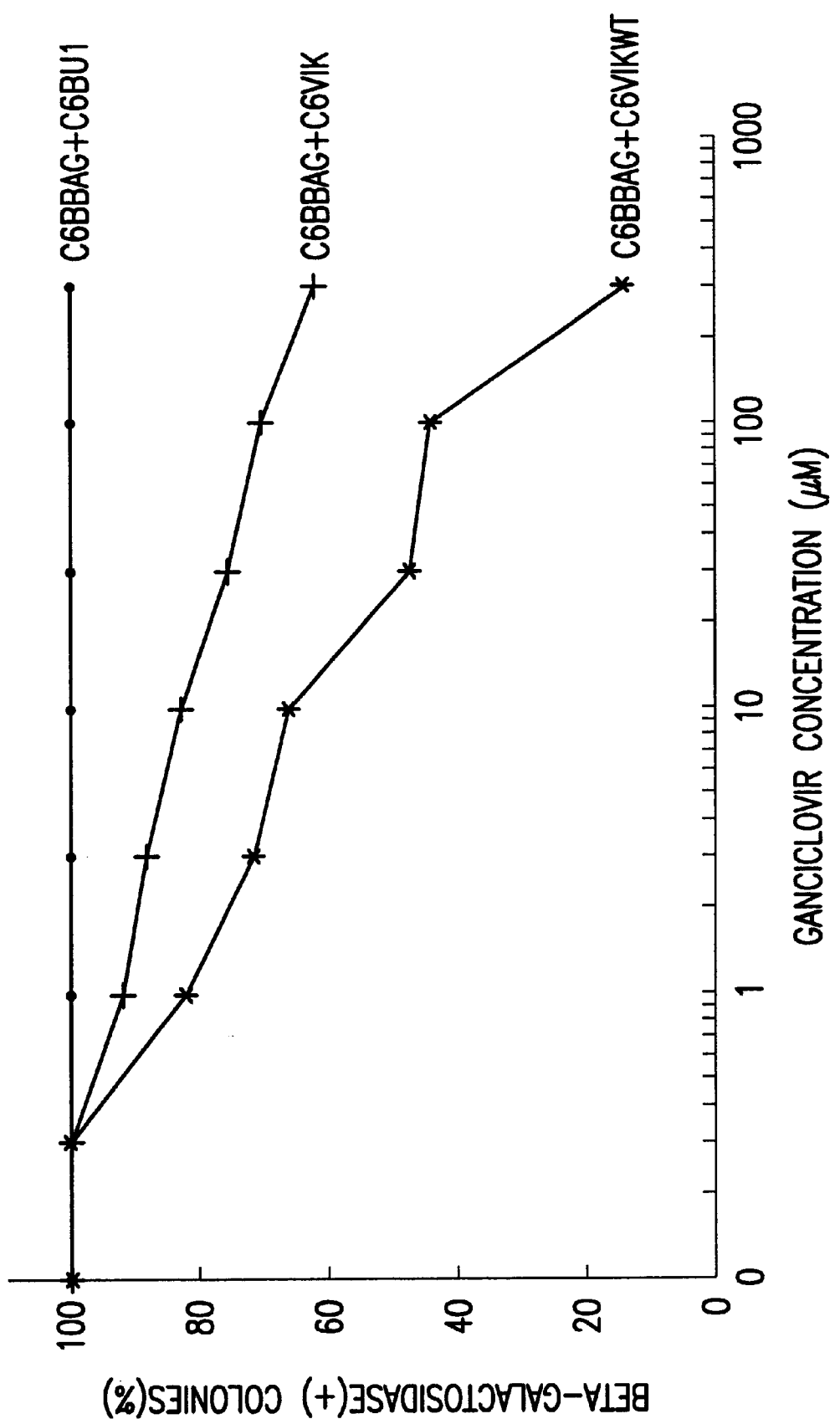
FIG. 6: Ganciclovir sensitivity of C6BAG cells after delayed co-culturing with other C6-derived lines. This analysis was carried out as in FIG. 5 except C6BBAG, which lack endogenous TK, were used instead of C6BAG. Studies were done in triplicate with less than 0.5% variability.

Co-culture experiments were undertaken to determine whether ganciclovir-sensitive "donor" cells carrying the HSV-TK gene, could transfer drug sensitivity to HSV-TK negative "recipient" cells. Sensitization of recipient cells was observed following co-culture with either C6VIK or C6VIKWT (in a ratio of 1:2) (FIG. 5), but the latter was much more effective, resulting in almost complete ablation of the recipient cells, as assessed by the percentage of surviving beta-galactosidase-positive colonies. In a parallel, control experiment, when C6BAG cells were co-cultured with either C6BU1 or C6BWT cells (ratio 1:2), no significant sensitization to ganciclovir was observed. In a similar experiment, recipient C6BBAG cells demonstrated a comparable higher ganciclovir sensitivity when co-cultured with C6VIKWT cells as compared with C6VIK cells. However, the dose of ganciclovir needed to inhibit colony formation by C6BBAG cells was higher than for C6BAG cells (FIG. 6). For example, in co-cultures with C6VIKWT cells, 50% of C6BAG cells grew when in the presence of 3 μM ganciclovir, while 50% of C6BBAG cells grew at 30 μM ganciclovir. This higher sensitivity of C6BAG cells is due to their endogenous thymidine kinase activity, which is lacking in C6BBAG cells.

Figure 7:
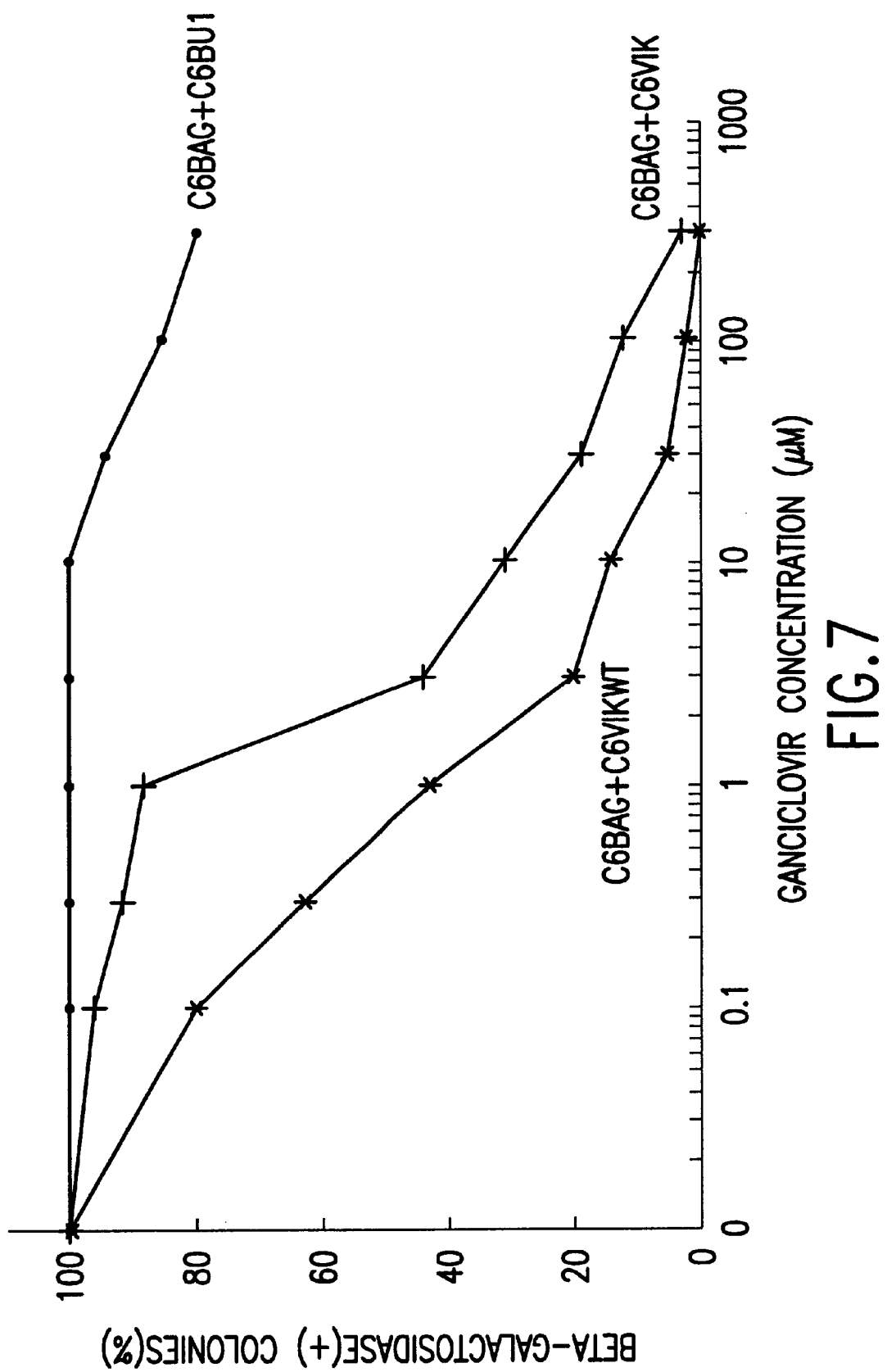
FIG. 7: Ganciclovir sensitivity of C6BAG cells after simultaneous co-culture with other C6-derived lines. Simultaneous co-culture experiment with C6BAG cells as recipients and C6VIK and C6VIKWT cells as donors (1:100). Ganciclovir treatment was begun seven days after plating and continued for 14 days. Only beta-galactosidase positive colonies were counted (see FIGS. 5 and 6). Studies were done in triplicate with less than 0.5% variability.
Figure 8:
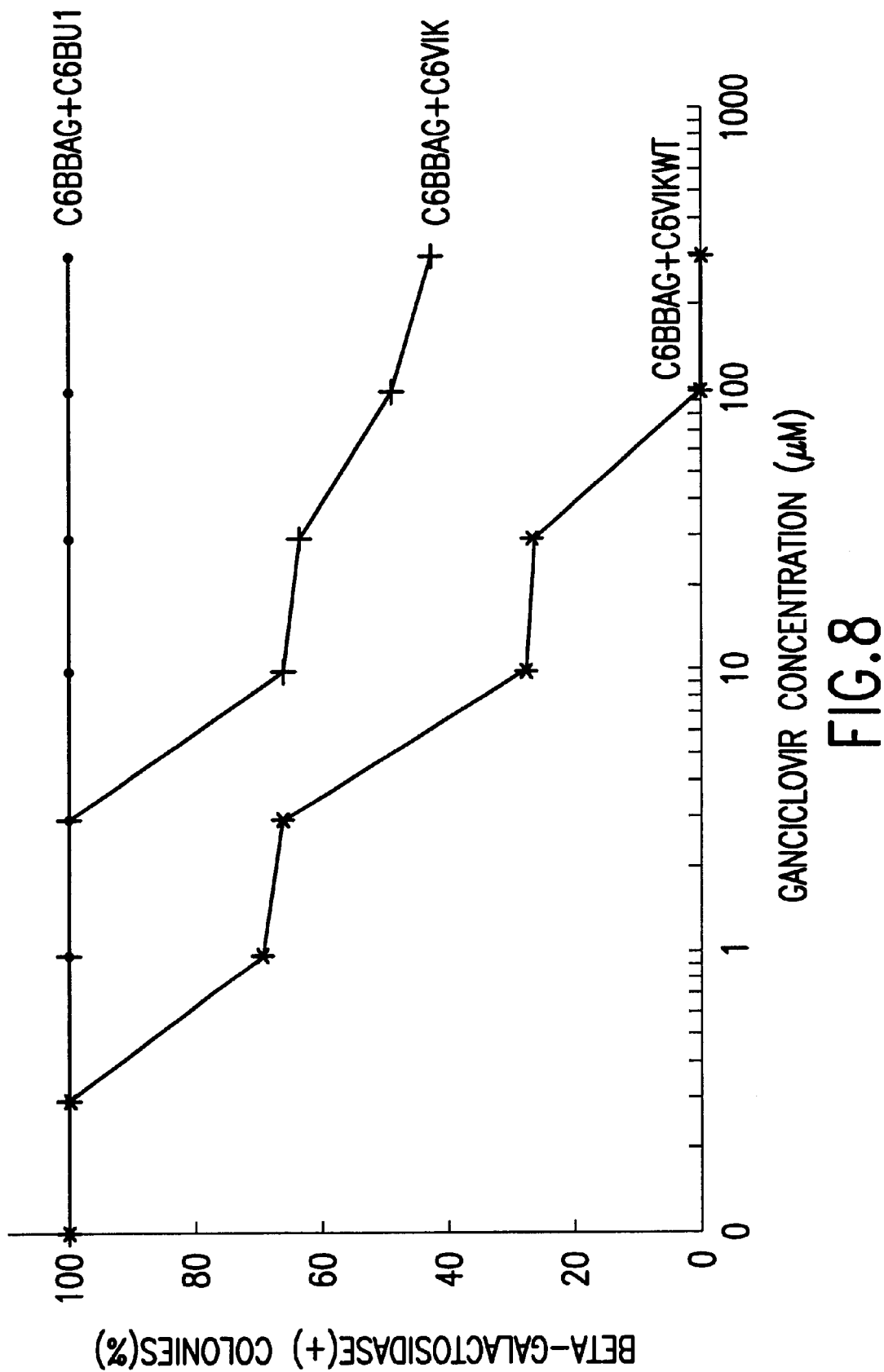
FIG. 8: Ganciclovir sensitivity of C6BAG cells after simultaneous co-culture with other C6-derived lines. Simultaneous co-cultures experiments with C6BBAG cells carried out as in FIG. 7. Studies were done in triplicate with less than 0.5%. variability.
Figure 9:
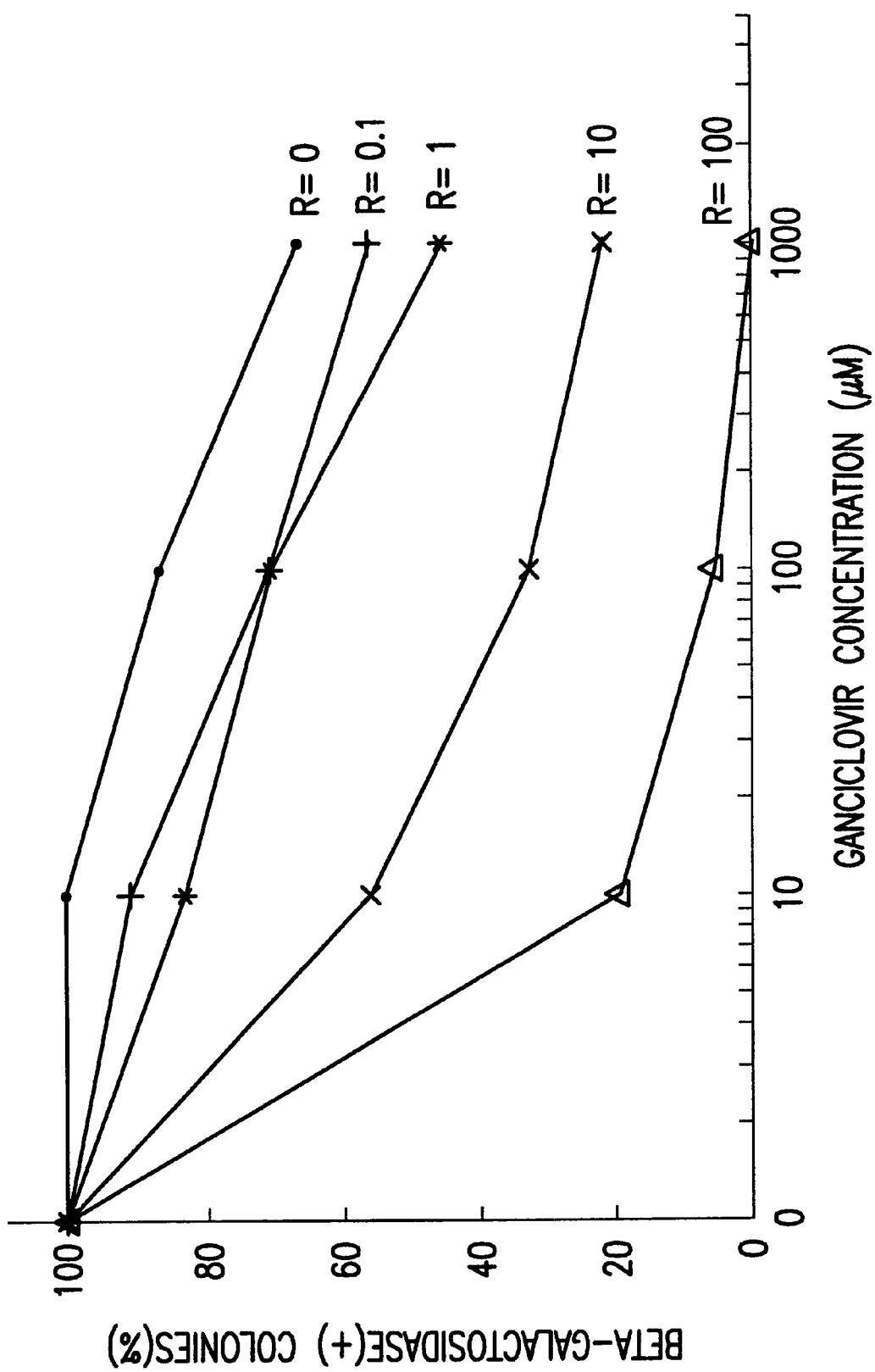
FIG. 9: Simultaneous co-culture experiments using varying ratios of donor C6VIKWT, to recipient cells C6BAG. Experiments were carried out as described in the legend to FIGS. 7 and 8. Studies were done in triplicate with less than 0.5% variability.

In co-culture experiments in which recipient C6BAG cells (FIG. 7) or C6BBAG cells (FIG. 8) were plated simultaneously with donor C6VIK or C6VIKWT cells (in a ratio of 1:100) greater sensitization of C6BAG cells to ganciclovir was seen in the presence of C6VIKWT cells as compared to C6VIK cells (FIG. 7). In these simultaneously plated co-cultures the ganciclovir sensitivity of C6BAG cells appeared to be 10-fold greater than in delayed co-cultures. This may reflect the ratio of donor cells to recipient cells which was 50-fold greater in the simultaneous experiments. The effect of cell ratios was investigated by changing the proportion of donor cells (C6VIKWT) to recipient cells (C6BAG). At 100 μM ganciclovir in ratios of 0.1 and 1, there was no significant difference in the ganciclovir sensitivity of C6BAG cells as compared to cultures of C6BAG cells alone. At ratios of 10 and 100 there was a "dose response" curve of greater sensitivity to 100 μM ganciclovir of C6BAG cells with increasing numbers of C6VIKWT cells (FIG. 9). In subsequent in vivo experiments, a ratio of 10:1 was used for donor cells: recipient cells.

Assays of *Gene Transfer*

Medium from the. wild type-infected line, C6VIKWT, was used to titrate transfer of the HSV-TK gene to NIH3T3 (TK⁻) cells and the neo$^R$ gene to NIH3T3 cells. The titer for G418 resistance was 5×10$^5$ cfu/ml on NIH3T3 cells. The titer of TK gene transfer as assessed by HAT resistance of LMTK⁻ cells was 3.2×10$^3$ cfu/ml. The higher titer of vector yielding G418 resistance, as compared to that for HAT resistance, reflects the greater sensitivity of this assay and/or greater expression of the neoR gene. This high titer indicates that the WT virus, which was not assayed directly, was actually replicating in C6VIKWT cells.

Toxicity Assay

Conditioned medium obtained from C6VIKWT cultures, before and during 300 μM ganciclovir treatment, was assayed on naive C6BU1 cells by the colony survival method. No apparent growth inhibition was noted, indicating that if toxic substances were released into the medium, they were not effective against these naive cells (data not shown).

In vivo Experiments

Ganciclovir Sensitivity of C6VIKWT

Figure 10:
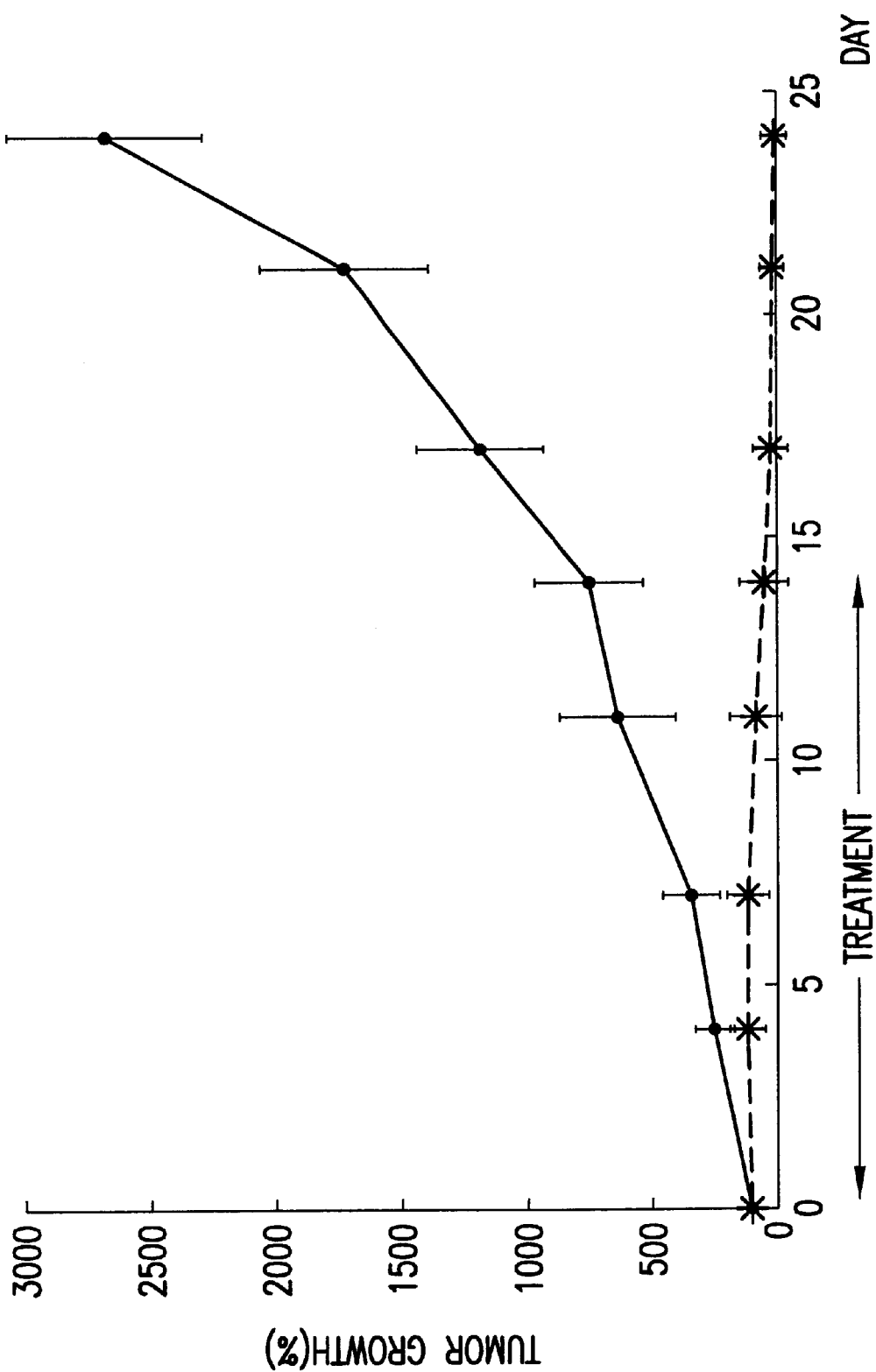
FIG. 10: Growth of subcutaneous C6VIKWT tumors in nude mice. Treatment was begun after the tumor size had reached 1 cm in diameter (day 0) and continued for 14 days. The tumor growth rate (%) was calculated in comparison with the initial volume (100% at day 0). Tumors were treated with PBS (solid line) or with 50 mg/kg/day ganciclovir (dotted line). Bars indicate standard error of the mean.

Subcutaneous injection of C6VIKWT cells into the flank of nude mice produced tumor masses which increased in volume on average over 27-fold during a 24 day period (FIG. 10). The growth rate was slower for cells, which were infected with wild type virus, than that observed previously for uninfected C6VIK cells (Ezzedine et al., *New Biol.* 3:608–614 (1991)). Treatment of C6VIKWT tumors with ganciclovir for 14 days, beginning after the tumor had reached a size of 1 cm in diameter, inhibited subsequent growth completely (FIG. 10). There was no apparent difference in inhibition kinetics in the three ganciclovir regimens tested; 50 mg/kg/day ganciclovir in two injections per day regimen, 50 mg/kg/day in one injection per day regimen, or 25 mg/kg/day in two injections per day (data not shown). In all 13 animals in which ganciclovir treatment was stopped after 14 days, slow regrowth of tumors occurred over the next two weeks (data not shown).

Figure 11:
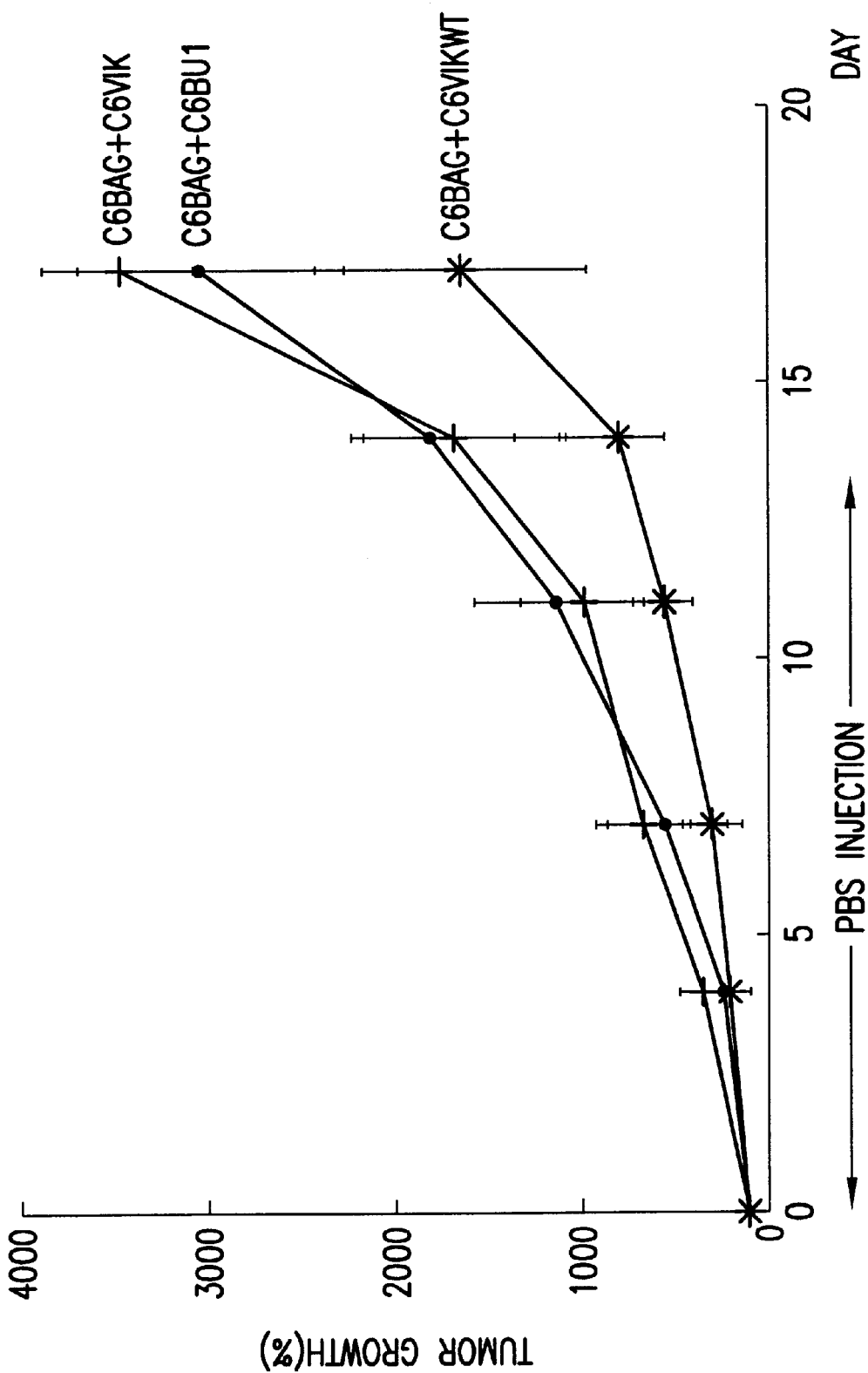
FIG. 11: Growth of combinations of tumor cells in nude mice. Tumor cells were inoculated simultaneously in different combinations in a ratio of 1 to 10 (recipient (C6BAG) versus donors C6BU1(n=9), C6VIK (n=9) or C6VIKWT, (n=7)). After tumors reached 1 cm in diameter, animals were treated with PBS for 14 days and then maintained without treatment for an additional 4 days. Bars indicate standard error of the mean.
Figure 12:
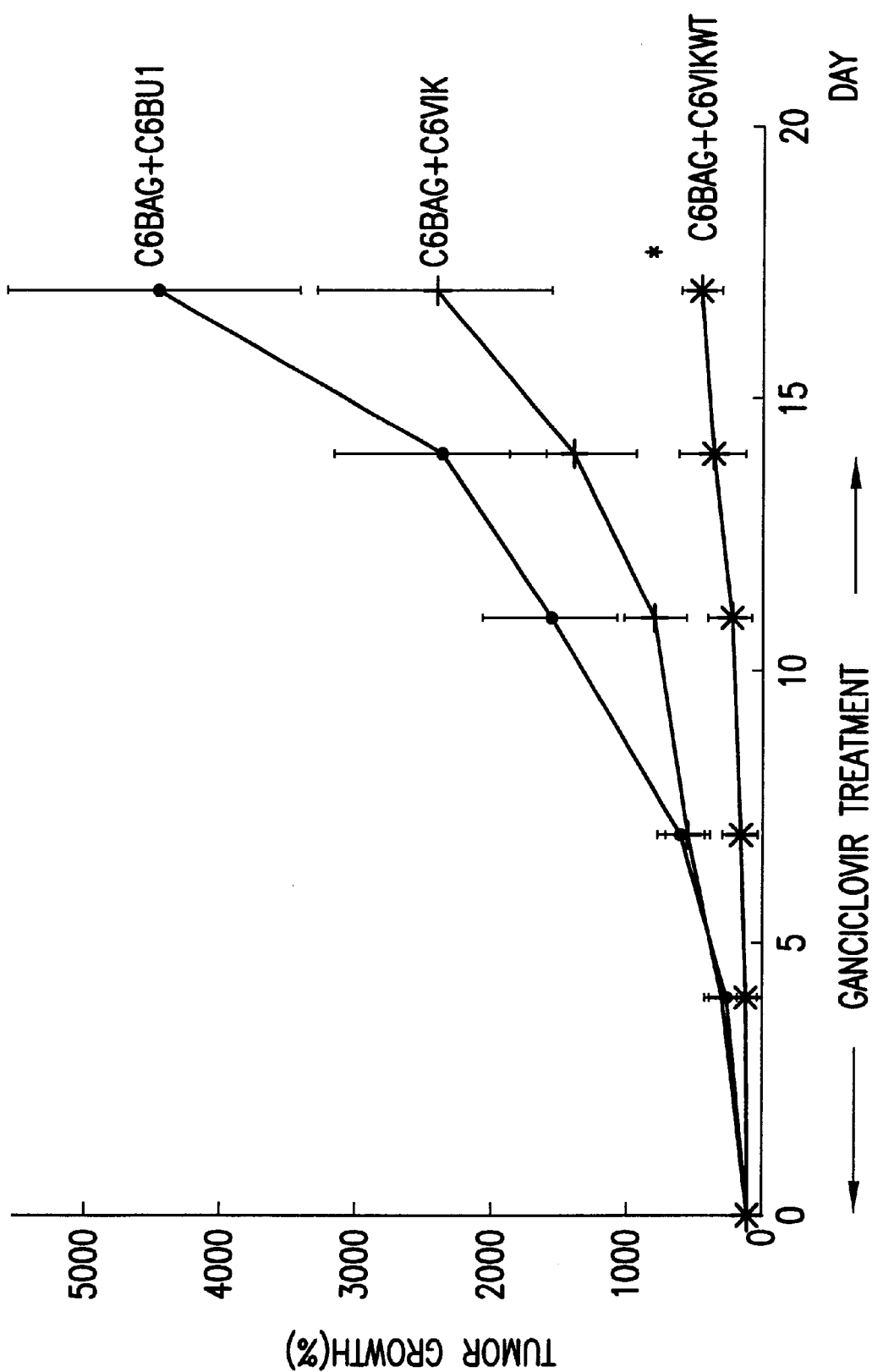
FIG. 12: Growth of combinations of tumor cells in nude mice. The same combinations of cells as in FIG. 11 were treated in parallel with 50 mg/kg/day ganciclovir for 14 days. *=p<0.01. Bars indicate standard error of the mean.

When different combinations of cells were tested, there was no significant difference in the volume of tumors in the animals receiving both C6BAG and C6BU1 cells, or C6BAG and C6VIK cells during 14 days treatment with PBS (FIG. 11). Tumors which represented a combination of C6BAG and C6VIKWT cells (1:10); however, were smaller at all time points over this period. In parallel, animals bearing such tumors received a 14 day course of ganciclovir treatment. There was a significant decrease in the tumor volume of those composed of C6BAG and C6VIK cells as compared to those containing C6BAG and C6BU1 cells over this period, and an even greater decrease in the size of C6BAG and C6VIKWT tumors (FIG. 12). Histologic examination of the latter tumors at day 17 revealed extensive necrosis and it was not possible to determine the identity of any remaining tumor cells (data not shown). Again, there was a slow regrowth of this latter tumor cell combination over a subsequent two-week period, and this regrowth was not blocked by another two weeks of ganciclovir therapy (data not shown). The surviving tumor might consist of C6BAG cells which did not receive the HSV-TK gene or C6-derived cells bearing this gene in which its expression was "shut-off."

Discussion

It has been demonstrated that the efficacy of retrovirus-mediated gene transfer and the chemosensitivity to the nucleoside analogue, ganciclovir, can be increased in glioma cells by combined infection with a retrovirus vector containing the HSV-TK gene and wild type MoMLV. This treatment was effective at killing tumor cells both in culture and in vivo.

Gene therapy is a new and potentially powerful approach to treatment of cancer and other disorders (Gansbacher et al., *Cancer Res.* 50:7820–7825 (1990); Rosenberg, *Cancer Res.* 51:5074s–5079s (1991); Gilboa, E., "Retroviral Gene Transfer: Applications to Human Therapy" , in: *Biology of Hematopoiesis,* Wiley-Liss Inc., pp. 301–311 (1990)). Tumor cells infected with retrovirus vectors bearing the HSV-TK gene can be eradicated by administration of ganciclovir (Moolten, *Cancer Res.* 46:5276–5281 (1986); Moolten et al., Human Gene Ther. 1: 125–134 (1990); Moolten and Wells, *J. Natl. Cancer Inst.* 82:297–300 (1990); Plautz et al., *New Biol.* 3:709–715 (1991)). Retrovirus infection requires cell division, and the target cells in the normal adult CNS are reported to be glia and endothelial cells (Kay, D. G., et al., *Proc. Natl. Acad. Sci. USA* 88:1281–1285 (1991)). Neurons can only be infected in the prenatal period, when neuroblasts are actively dividing (Sharpe, A. H., et al., *Nature* 346:181–183 (1990)). Brain tumors constitute masses of dividing cells within a background of mostly non-dividing host cells and should be ideal candidates for targeted gene therapy by retrovirus vectors. The selective chemosensitization of rat C6 glioma cells in culture and in vivo using a similar retrovirus vector, VIK, has been reported (Ezzedine, Z. D., et al., *New Biol.* 3:608–614 (1991)). Rat C6 glioma cells infected with this vector and cloned in culture, C6VIK cells, were introduced subcutaneously into nude mice. Subsequent treatment of the animals with ganciclovir inhibited tumor growth of C6VIK cells, but had no effect on tumor growth of parental C6 cells.

Presently, it has been demonstrated that chemosensitivity to the nucleoside analogue, ganciclovir, can be increased in glioma cells by combined infection with a retrovirus bearing the HSV-TK gene and with wild type MoMLV. This treatment was effective at killing C6 tumor cells both in culture and in vivo. Even more strikingly, this effect can be transferred to "naive" (i.e., uninfected) C6 glioma cells.

In order to treat an actual tumor, transfer of the gene needs to take place in vivo. Previously, a producer cell line (mouse fibroblast-derived), releasing the reporter retrovirus vector, BAG, was implanted near a tumor bed of C6 glioma cells in the adult rat brain. This yielded a level of gene transfer to tumor cells of about 10%. However, the period of gene delivery was curtailed by immune rejection of the vector-producing line.

Presently, the duration of vector-mediated gene delivery to tumor cells has been extended in two ways. First, C6VIK glioma cells were superinfected with a "helper" wild type MoMLV. These C6VIKWT cells release both wild type virus and replication-defective virus vectors containing the HSV-TK gene, both of which can infect neighboring tumor cells, provided the latter are proliferatively active. Proliferation is a prerequisite for retrovirus integration (Miller, D. G., et al., Mol. Cell Biol. 10:4239–4242 (1990)).

When neighboring cells are infected either sequentially or simultaneously with the vector and the wild type virus, they can, in turn, become "producer" cells able to release both the wild type virus and the vector to additional cells. This allows extended spread of vector production by dividing tumor cells in the brain, which are able to integrate retroviral DNA in the genome. These glioma-derived "producer" cells can migrate in the adult brain as do glioma cells (Burger et al., J. Neurosurg. 58:159–169 (1983)) and astrocytes (Jacque et al., Dev. Neurosci. 8:142–149 (1986); Zhou et al., J. Comp. Neurol. 292:320–330 (1990); Hatton et al., Soc. for Neurosci. Abstracts 15:1369 (1989)), and of intermingling with other tumor cells.

Another means to improve efficacy of gene transfer to glial tumors includes development of a glia-derived packaging line from the same strain in which the tumor is implanted or originates. Such cells will have increased longevity within the CNS and will also obviate the need for WT virus. The absence of WT virus will increase the safety of therapy. It will also remove a potential barrier to universal infection of recipient cells by the vector, since cells infected with the wild type virus are resistant to subsequent infection with either wild type virus or the vector, due to expression of envelope glycoproteins on their surface (Kabat, D., Curr. Top. Microbiol. Immunol 148:1–42 (1989)).

Presently, C6VIKWT cells (C6 glioma cells bearing the HSV-TK gene, superinfected with MoMLV virus) were significantly more sensitive to. ganciclovir than parental C6VIK cells. This effect is specific to the presence of the HSV-TK gene since C6BU1 cells infected with the MoMLV did not show any greater sensitivity than the parental cell line, C6BU1. This difference in sensitivity between C6VIK and C6VIKWT cells was even greater when assessed by a colony assay. The difference in sensitivity observed using these two assays may reflect a lower sensitivity of isolated cells as compared to those in colonies. Close cell contacts within cells in colonies may increase the transfer of HSV-TK gene allowing multiple integrations per cell or may increase the intracellular concentration of ganciclovir or toxic metabolites derived from it. The effectiveness of C6VIKWT cells was also apparent in their ability to sensitize recipient cells to ganciclovir, as evidenced by co-culture of recipient cells marked: with the lacZ gene, C6BAG or C6BBAG cells, and donor cells, C6VIK or C6VIKWT. Since there was no significant difference in the ganciclovir sensitivity of C6BU1 and C6BWT cells, the transfer of the HSV-TK gene in the presence of wild type virus, rather than the wild type virus alone, is responsible for this killing effect. However, some transfer of ganciclovir sensitivity to recipient cells was seen with the C6VIK donor (i.e., even in the absence of WT virus). As a consequence, several assays were done to determine whether the increased sensitivity of recipient cells to ganciclovir was due to transfer of the TK gene, infection with wild type retrovirus and/or the release of a toxic metabolite. Medium from cocultures was titered for VIK retrovirus and tested for toxicity to naive cells. Assays for gene transfer mediated by media from C6VIKWT cells documented the presence of vectors bearing the neomycin resistance gene and TK gene. No toxicity was noted when naive C6BU1 cells were exposed to media from cultures of C6VIKWT cells with or without ganciclovir treatment. This does not exclude the possibility that sensitivity in the absence of WT virus might be mediated by direct transfer of toxic metabolites by donor cells to recipient cells through cell-to-cell contacts, but suggests that these metabolites are not exchanged through the medium.

The extraordinary chemosensitivity of C6VIKWT cells to ganciclovir was apparent in vivo as well as in culture. The presence of wild type virus contributed to the sensitivity of these cells, as treatment of subcutaneous C6VIKWT tumors with ganciclovir completely blocked tumor growth, whereas in previous studies C6VIK tumors treated with ganciclovir continued to grow at a slow rate (Ezzedine, Z. D., et al., New Biol. 3:608–614 (1991)). C6VIKWT tumors grow more slowly than C6VIK tumors, suggesting that wild type retrovirus itself may interfere with the growth of tumor cells. However, injection of the WT MoMLV into subcutaneous C6 tumors appears to have no effect on tumor growth (Y. Takamiya, unpublished data). It has been shown that wild type retrovirus infection can affect the differentiated phenotype of cultured human glioma cell lines (Macchi, B., et al., Acta Neuropathol. 81:670–674 (1991)), but it is not clear whether this alters the tumorigenicity of these cells. Co-injection of C6BAG and C6VIKWT cells followed by treatment with ganciclovir revealed a markedly reduced rate of tumor growth as compared with combinations of C6BAG and either C6BU1 or C6VIK cells, with no residual tumor cells seen histologically after therapy. This result is consistent with the transfer of the HSV-TK gene to recipient C6BAG tumor cells was mediated by production of the VIK vector by adjacent C6VIKWT cells.

Although wild type MoMLV can cause leukemia and neuropathic effects in young mice (Sharpe, A. H., et al., Nature 346:181–183 (1990); Kay, D. G., et al., Proc. Natl. Acad. Sci. USA 88:1281–1285 (1991)), immune competent adult mice are quite resistant to the pathogenicity of this virus. The present in vivo data reported here, were obtained using nude mice which are immunocompromised (Gullino, P. M., et al., Institute Lab Animal Resources (ILAR) News 19:M1–M20 (1976)), although in this study all pathogenicity in animals appeared to be related to tumor growth in the brain.

Figure 13:
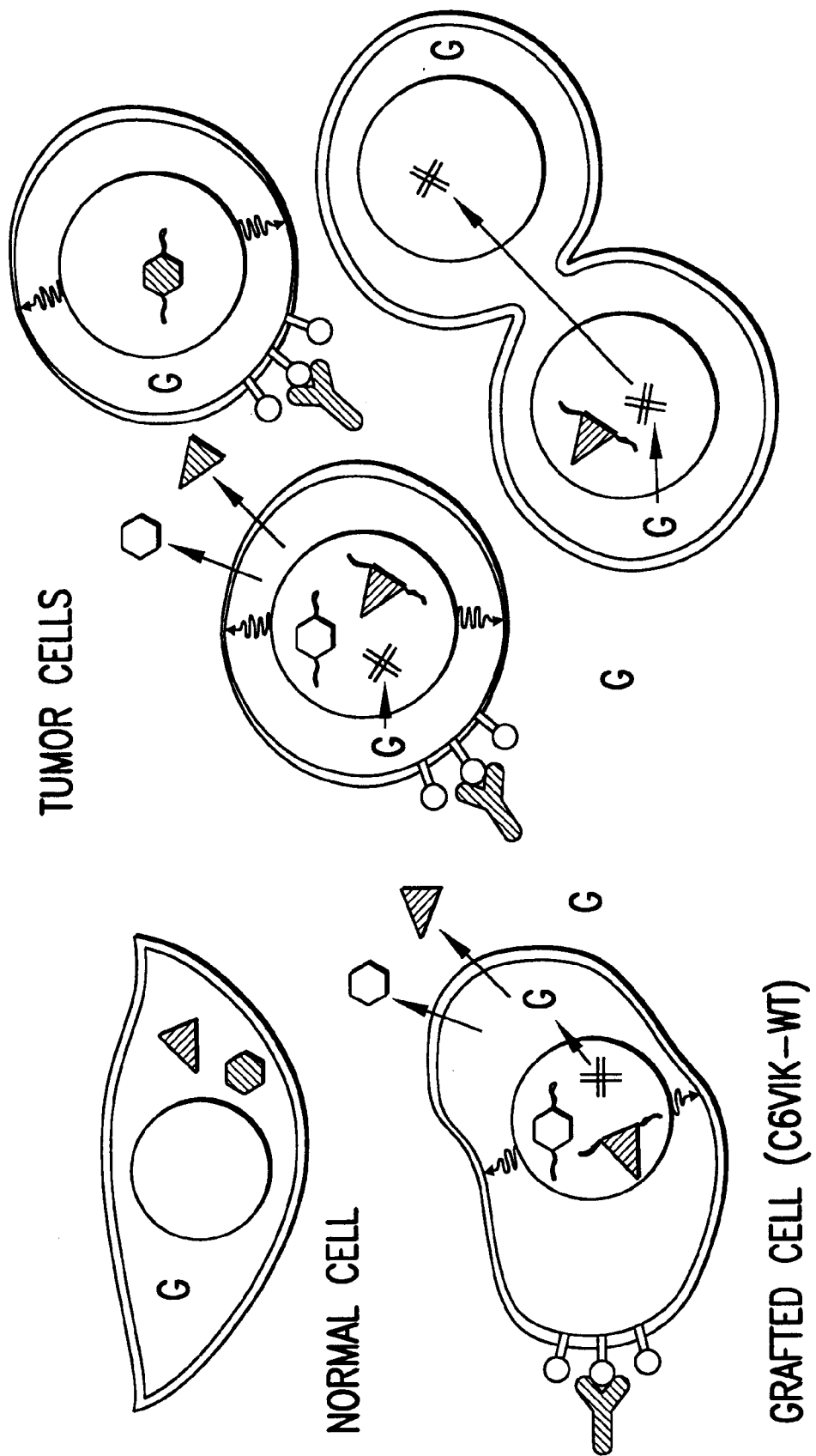
FIG. 13. Toxic effects of C6VIKWT on tumor cells. In the adult brain, most normal cells are not dividing and thus resistant to integration of retroviruses and toxic ganciclovir metabolites. Toxic effects of grafted C6VIKWT cells on dividing tumor cells may include: 1) debilitating effects (~>) of replicative infection of wild type MoMLV (hexagon); 2) expression of viral antigens on cells (♦)which trigger rejection by host antibodies or other immune mechanisms (λ); 3) integration of retrovirus vector (Δ) bearing HSV-TK gene and conversion of ganciclovir (G) to a toxic metabolite (X) which kills cells undergoing DNA replication; and 4) transfer of X from infected tumor cells to uninfected tumor cells through cell contacts.

The ganciclovir sensitivity of glioma cells infected with both a retrovirus vector bearing the HSV-TK gene and wild type MoMLV virus, as well as their ability to transfer sensitivity to "naive" cells in their vicinity could be mediated by several factors as schematized in FIG. 13. These include the cellular debilitating effects of wild type retrovirus infection; host production of antibodies in response to viral and tumor antigens (in immune competent animals); integration and expression of the HSV-TK gene in tumor cells, allowing the cells to generate toxic metabolites from ganciclovir; and possible transfer of these toxic metabolites to neighboring cells. A gene therapy strategy utilizing this system thus provides four separate and additive means to kill tumor cells, all of which have no effect on endogenous brain cells. Cells bearing the HSV-TK gene also show increased sensitivity to radiation in the presence of ganciclovir, as its metabolites will interfere with DNA repair as well as DNA synthesis. Further extension of killing can be achieved by creating vectors bearing genes for secretable proteins, which selectively kill or inhibit growth of tumor cells, or for surface proteins which stimulate immune rejection of tumor cells. Several different vectors could thus be used in concert and combined with more traditional therapies.

Modifications of the above-described modes for carrying out the invention that are obvious to persons of skill in medicine, immunology, hybridoma technology, pharmacology, and/or related fields are intended to be within the scope of the following claims.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method for selectively transferring chemosensitivity to solid neoplastic cells, so that said cells may be killed, said method comprising:

(a) contacting said solid neoplastic cells with retrovirus vector—producing packaging cells, wherein the retrovirus vector produced by said packaging cells infects said solid neoplastic cells, said vector comprising a herpes simplex virus thymidine kinase gene whose gene product is capable of transferring chemosensitivity to said solid neoplastic cells;

(b) contacting said solid neoplastic cells with an agent which recognizes said gene product, thereby killing said solid neoplastic cells having chemosensitivity to said agent.

2. The method of claim 1, wherein said agent is ganciclovir, acyclovir, or FIAU.

3. The method of claim 2, wherein said agent is ganciclovir.

4. The method of claim 2, wherein said agent is acyclovir.

5. The method of claim 2, wherein said agent is FIAU.

6. The method of claim 1, wherein said retrovirus is VIK.

7. The method of claim 1, wherein said method further comprises co-infection of said neoplastic cells with a helper virus, wherein said helper virus is an ecotropic wild-type retrovirus.

8. A method for treating solid tumors in a host, said method comprising:

introducing retroviral vector-producing packaging cells into said solid tumor, wherein the retroviral vectors produced by said packaging cells infect tumor cells in said solid tumor, said vectors comprising a gene for herpes simplex virus thymidine kinase whose gene product kills the tumor cells upon interaction with an agent; and administering said agent to said host, thereby killing said infected solid tumor cells.

9. The method of claim 8, wherein said agent is ganiclovir, acyclovir, or FIAU.

* * * * *